United States Patent
Sharma et al.

(10) Patent No.: US 9,176,120 B2
(45) Date of Patent: Nov. 3, 2015

(54) SERUM-BASED, DIAGNOSTIC, BIOLOGICAL ASSAY TO PREDICT PREGNANCY DISORDERS

(75) Inventors: Surendra Sharma, Warwick, RI (US); Satyan Kalkunte, Providence, RI (US)

(73) Assignee: WOMEN & INFANTS' HOSPITAL OF RHODE ISLAND, Providence, RI (US)

( * ) Notice: Subject to any disclaimer, the term of this patent is extended or adjusted under 35 U.S.C. 154(b) by 1092 days.

(21) Appl. No.: 12/865,239

(22) PCT Filed: Feb. 4, 2009

(86) PCT No.: PCT/US2009/000708
§ 371 (c)(1),
(2), (4) Date: Nov. 9, 2010

(87) PCT Pub. No.: WO2009/099603
PCT Pub. Date: Aug. 13, 2009

(65) Prior Publication Data
US 2011/0059904 A1    Mar. 10, 2011

Related U.S. Application Data

(60) Provisional application No. 61/063,491, filed on Feb. 4, 2008.

(51) Int. Cl.
*C12Q 1/02* (2006.01)
*G01N 33/50* (2006.01)

(52) U.S. Cl.
CPC ...... *G01N 33/5091* (2013.01); *G01N 2800/368* (2013.01)

(58) Field of Classification Search
CPC ............... G01N 33/5091; G01N 2800/368
USPC ............................ 514/21.1; 435/29
See application file for complete search history.

(56) References Cited

U.S. PATENT DOCUMENTS

2005/0074746 A1* 4/2005 Mor et al. .................. 435/4

OTHER PUBLICATIONS

Wang et al., Placental Trophoblasts-derived factors diminish endothelial barrier function, The Journal of Clinical Endocrinology and Metabolism, vol. 89, 2004, p. 2421-2428.*
Ashton et al., Uterine spiral artery remodeling involves endothelial apoptosis induced by extravillous trophoblasts through Fas/FasL interactions, Arteriosclerosis, thrombosis and Vascular biology, vol. 25, 2005, p. 102-108.*
Aldo et al., "A Novel three-dimensional in vitro system to study trophoblast-endothelium cell interactions", In: Amer. J. Reprod. Immunol., Aug. 2007, vol. 58, No. 2, Abstract.
Ganapathy et al., "Effect of first-trimester serum from pregnant women with high-resistance uterine artery Doppler resistance on extravillous trophoblast invasion", In: Hum Reproduction; May 2006, vol. 21, No. 5, pp. 1295-1298.
Renaud et al., "Coordinated regulation of human trophoblast invasiveness by macrophages and interleukin 10", In: Biol. Reprod., Mar. 2007, vol. 76, No. 3, Abstract.

* cited by examiner

*Primary Examiner* — Taeyoon Kim
*Assistant Examiner* — Tiffany Gough
(74) *Attorney, Agent, or Firm* — Novak Druce Connolly Bove + Quigg LLP

(57) ABSTRACT

The invention provides serum-based, diagnostic, biological assays for predicting disorders of pregnancy resulting from poor trophoblast and/or placental ischemia, including preeclampsia. Serum samples from such subjects exhibit an ability to disrupt the architecture involving fetal trophoblasts and maternal endothelial cells in a three-dimensional, dual cell co-culture system provided herein, in contrast to normal pregnancy serum samples. Based on these distinctions, the assays are employed to predict pregnancy outcomes as early as first trimester.

12 Claims, 17 Drawing Sheets

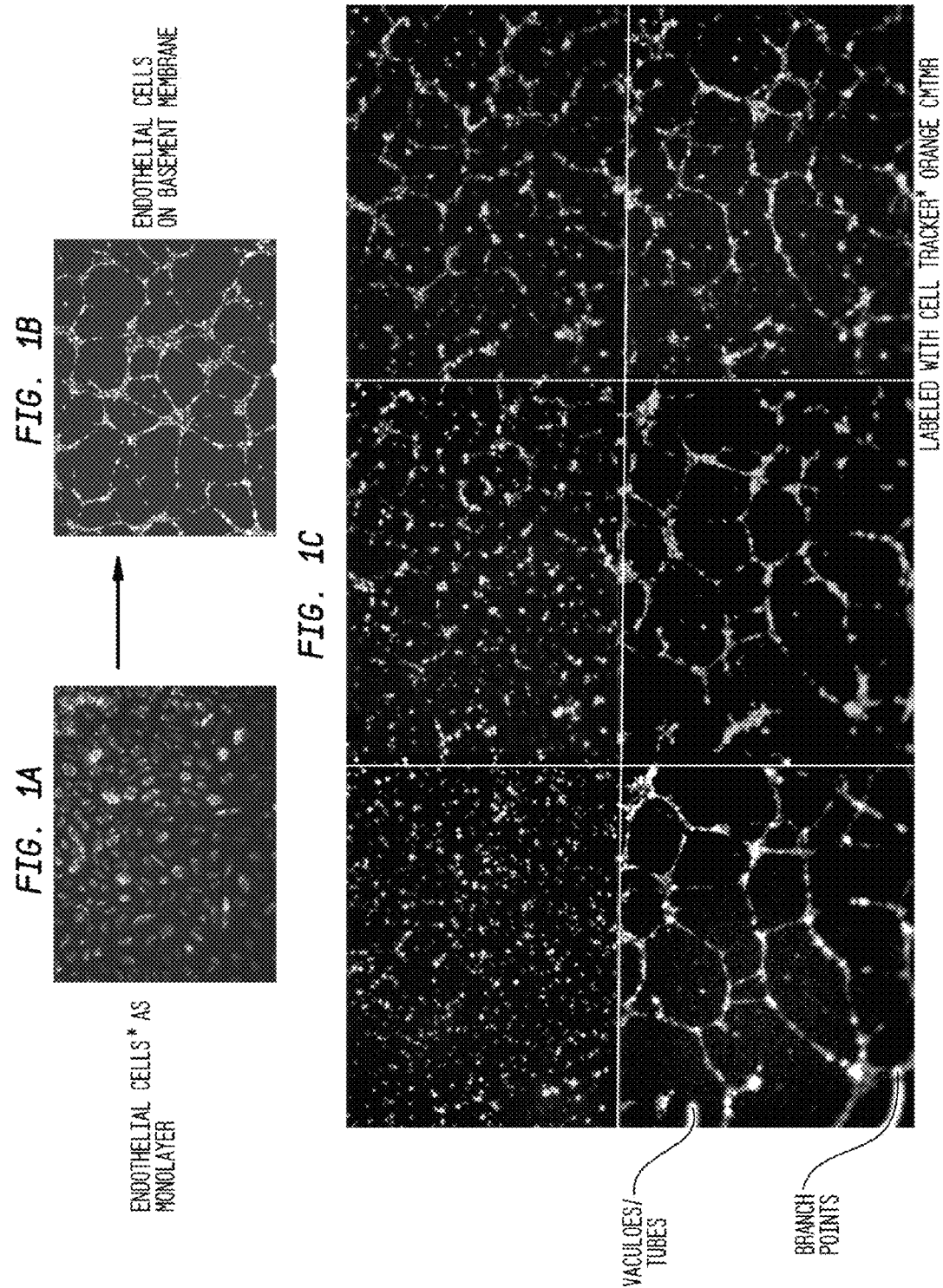

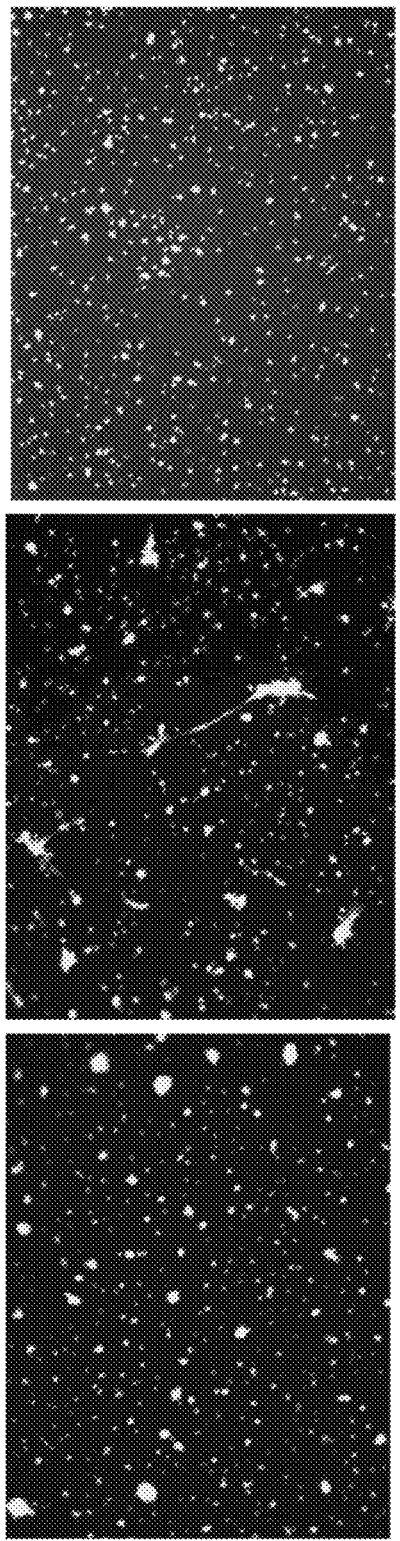

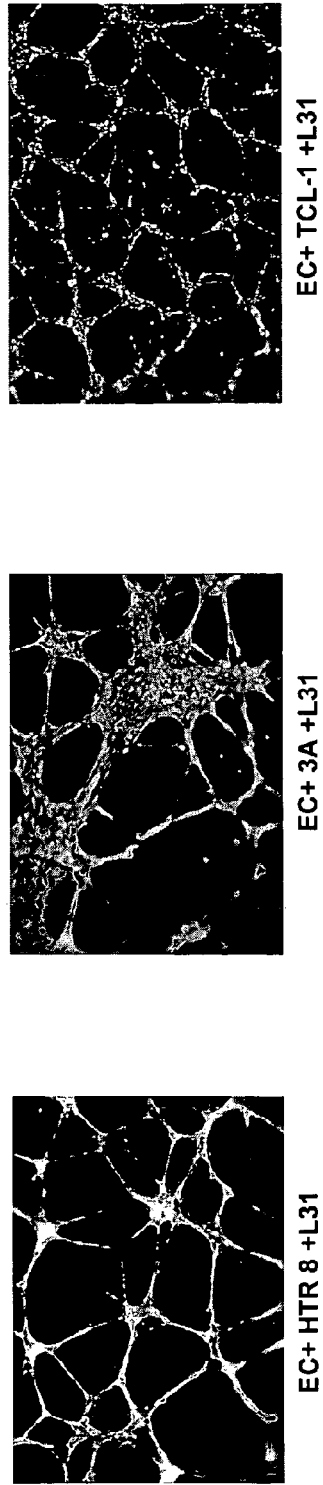
Fig 3. Normal pregnancy serum supports specific differential interaction with endothelial cells
Normal pregnancy serum supports "architectural imprinting" specifically in HTR8
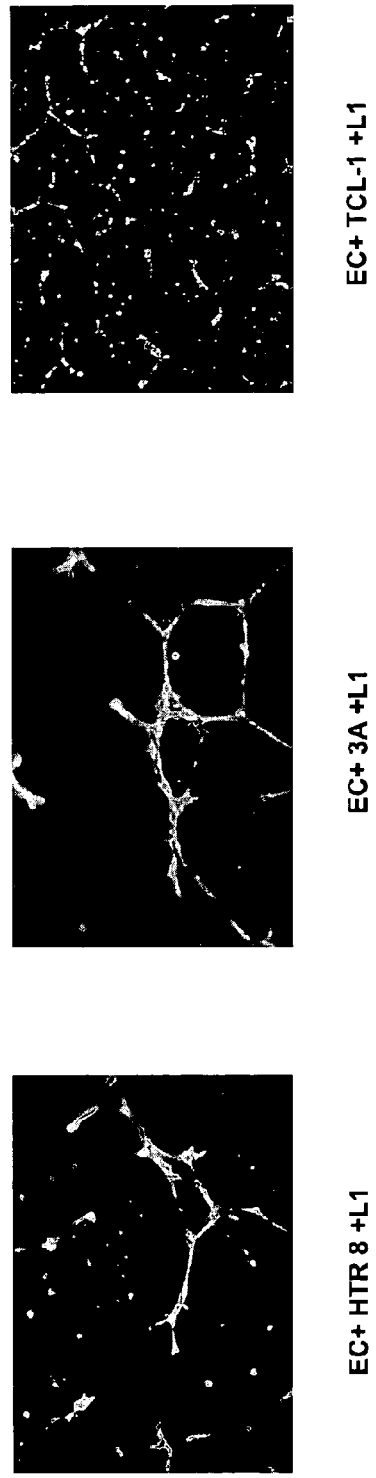
Fig 4. Pre-eclampsia serum disrupts gestational age specific differential interaction with endothelial cells

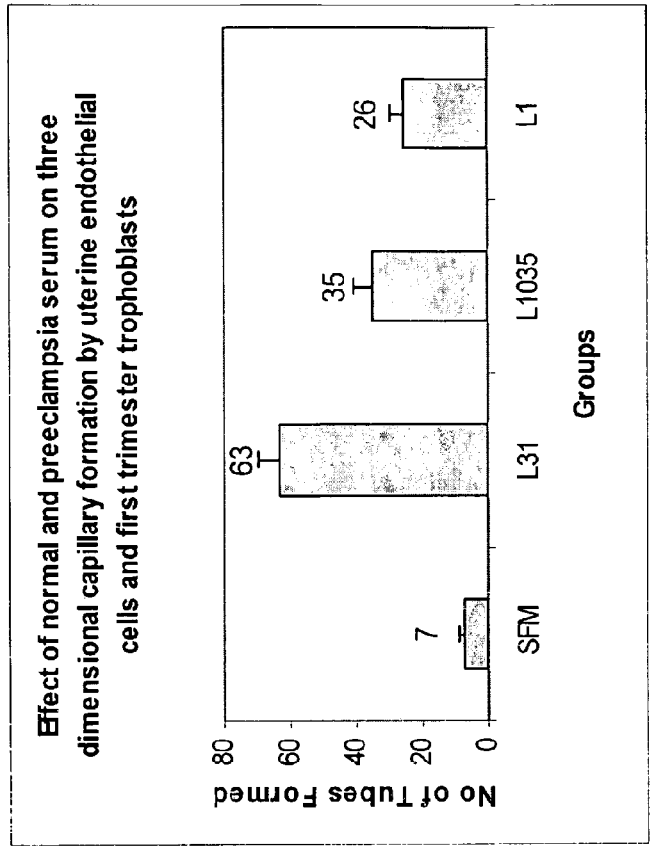
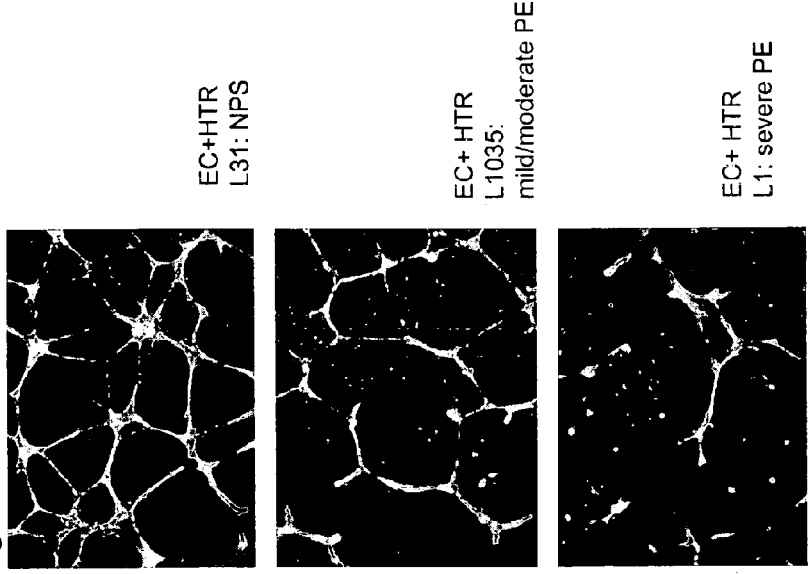
Fig 5: Quantitative effect of NPS, mild PE serum and severe PE serum on first trimester trophoblast-endothelial cell co-cultures on matrigel
Mild and Severe PE serum samples disrupt endothelial cell tube formation cross-talk with trophoblasts

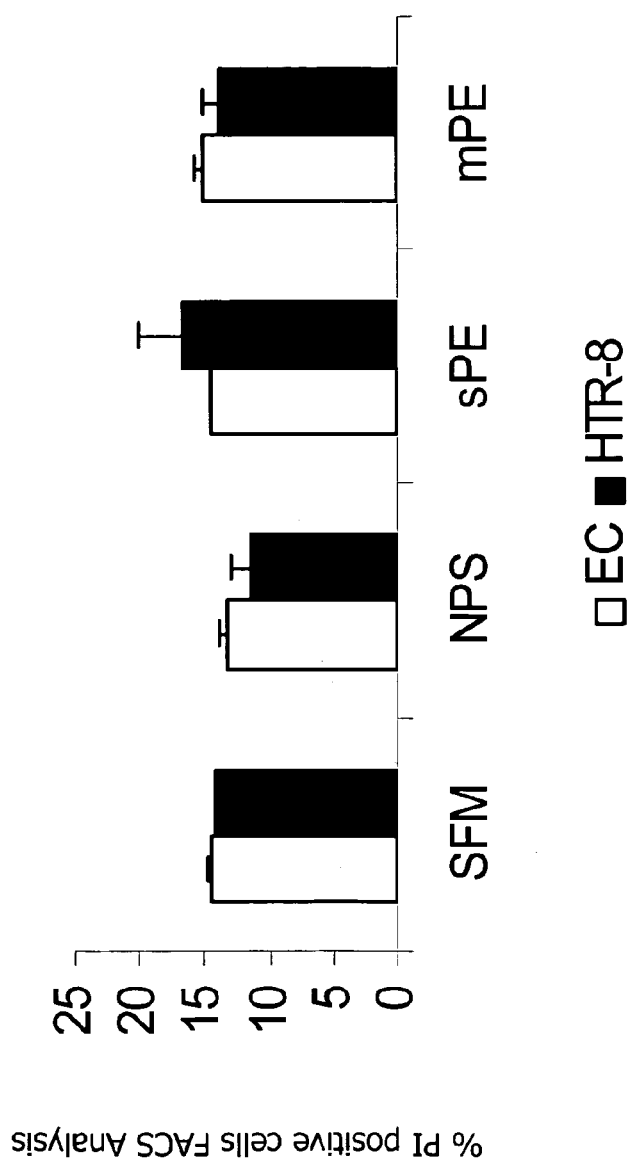
Fig 6. Effect of normal pregnancy serum (NPS), severe and mild preeclampsia serum (sPE or mPE) on trophoblasts and endothelial cell viability
Pre-eclampsia serum samples are non-cytotoxic to endothelial cells (EC) and first trimester trophoblasts (HTR8) as indicated by propidium iodide staining (PI)

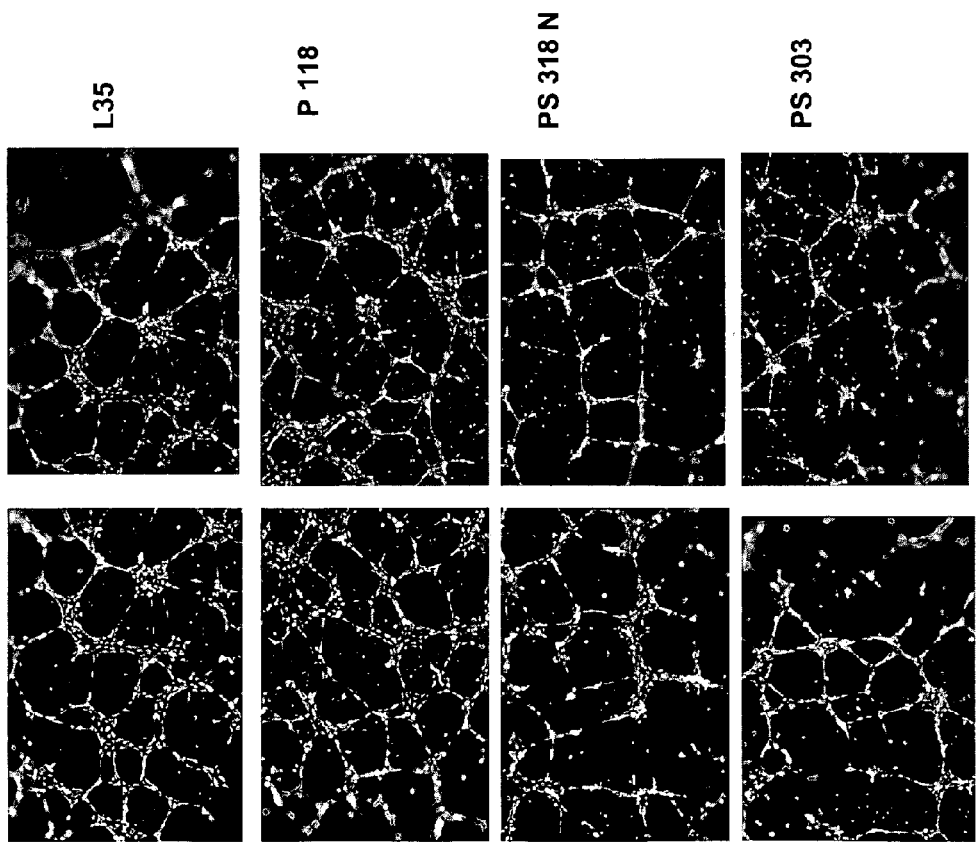
Fig 7a. Longitudinal studies with PE serum on endothelial-trophoblast cross-talk

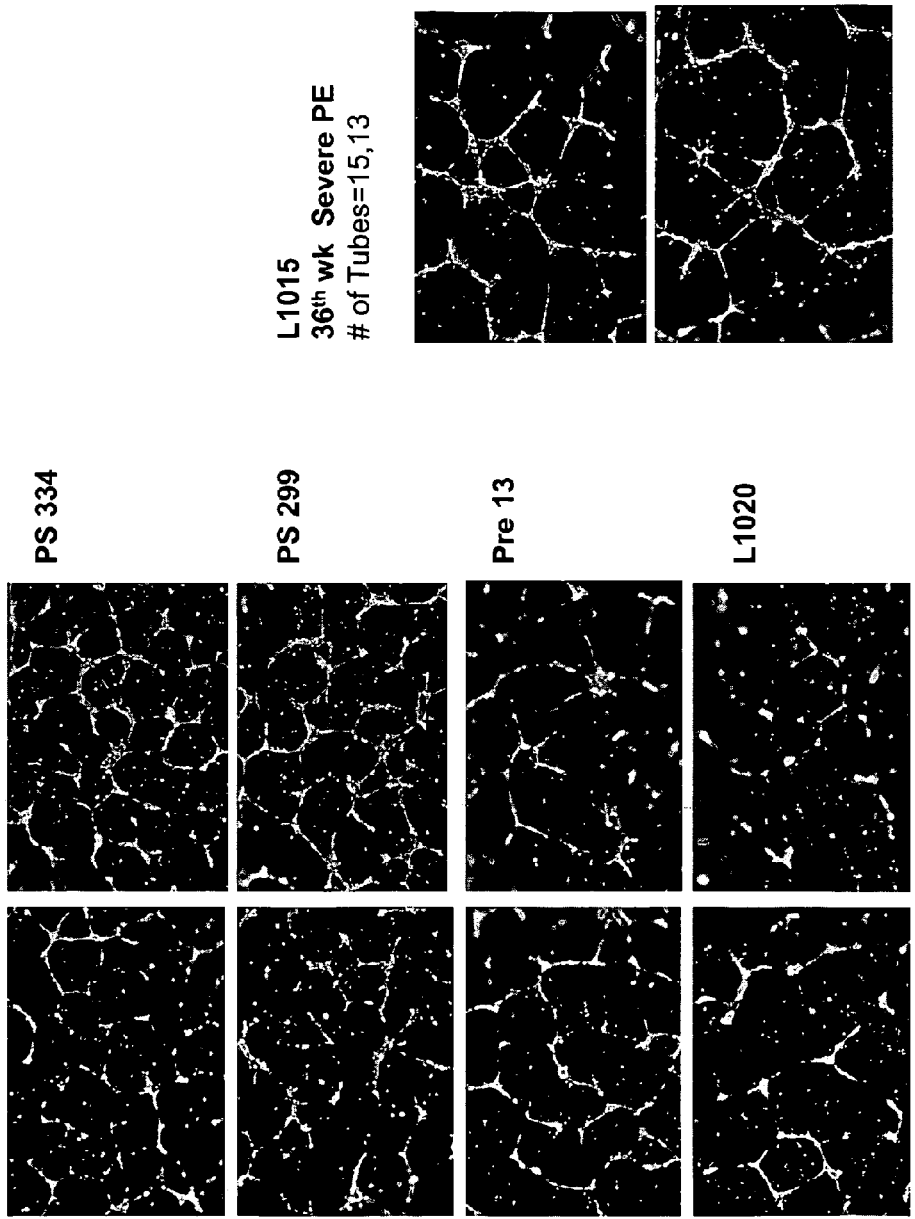

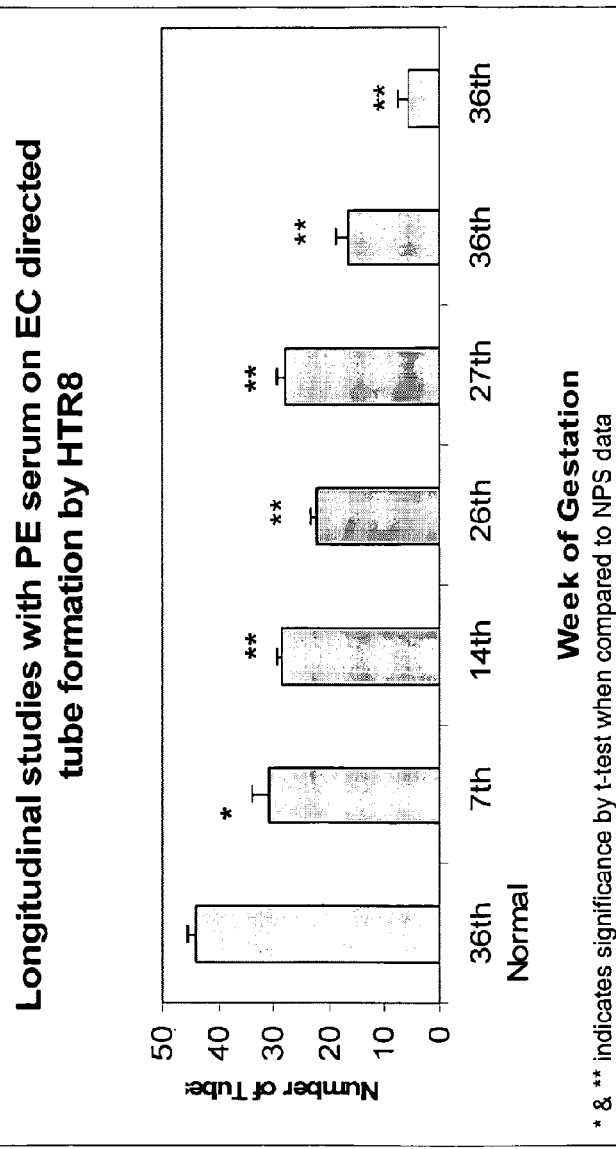
Fig 7c. Quantification of number of vacuoles/tubes formed in longitudinal studies with PE serum on endothelial-trophoblast cross-talk

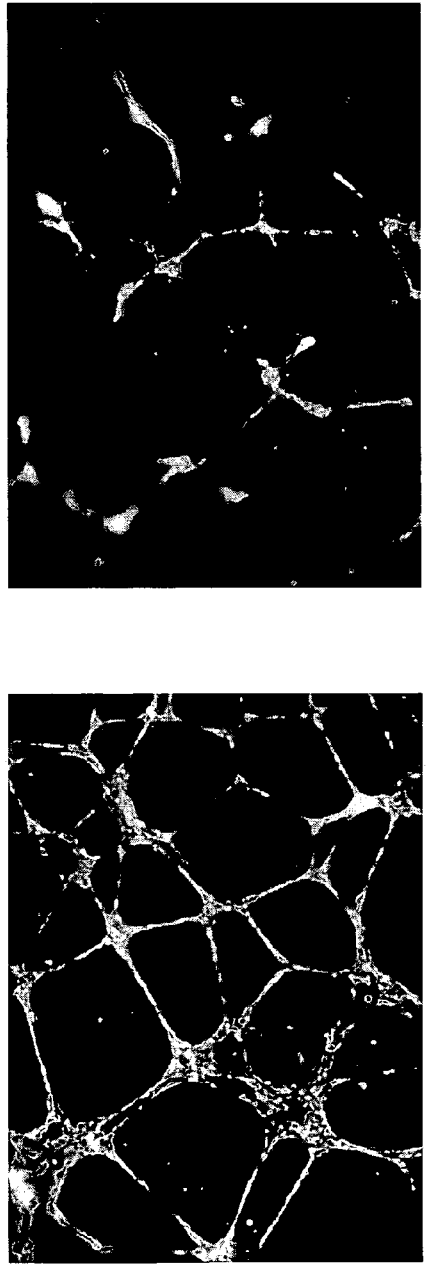
Fig 8a.: Complement split product C5a perturbs normal pregnancy serum induced cross-talk (vacuolization) between endothelial cells and trophoblasts
A: EC+HTR8+ L35 Normal Pregnancy Serum
B: EC+HTR8+L35+ C5a 100ng/ml
Neutralization or antagonist to C5a as "target" for therapeutic intervention

FIG. 8B

TABLE 2: COMPLEMENT SPLIT PRODUCT C5a LEVELS ARE ELEVATED ON SERUM SAMPLES FROM PRE-ECLAMPSIA

| | sEng(ng/ml) | sFlt-1(ng/ml) | C5a(ng/ml) |
|---|---|---|---|
| NORMAL | 16.93 ± 18.17 | 4.4 ± 4.33 | 29.77 ± 29.19 |
| MIXED PE POPULATION | 45.88 ± 41.38** | 21.43 ± 11.6** | 53.44 ± 37.73a |
| SEVERE | 56.68 ± 38.26** | 26.89 ± 11.92** | 57.94 ± 30.14b |
| MILD | 41.38 ± 42.57a | 19.15 ± 10.91** | 51.57 ± 40.92 |
| EARLY ONSET | 67.56 ± 45.00a | 25.57 ± 14.76** | 48.91 ± 22.53c |
| LATE ONSET | 39.21 ± 37.94a | 20.15 ± 10.26** | 54.84 ± 40.77a |

ALL VALUES ARE EXPRESSED AS MEAN +/- sd. **,a,b,c
INDICATES STATISTICAL SIGNIFICANCE AT P<0.001, P<0.01,
P<0.02, P<0.07

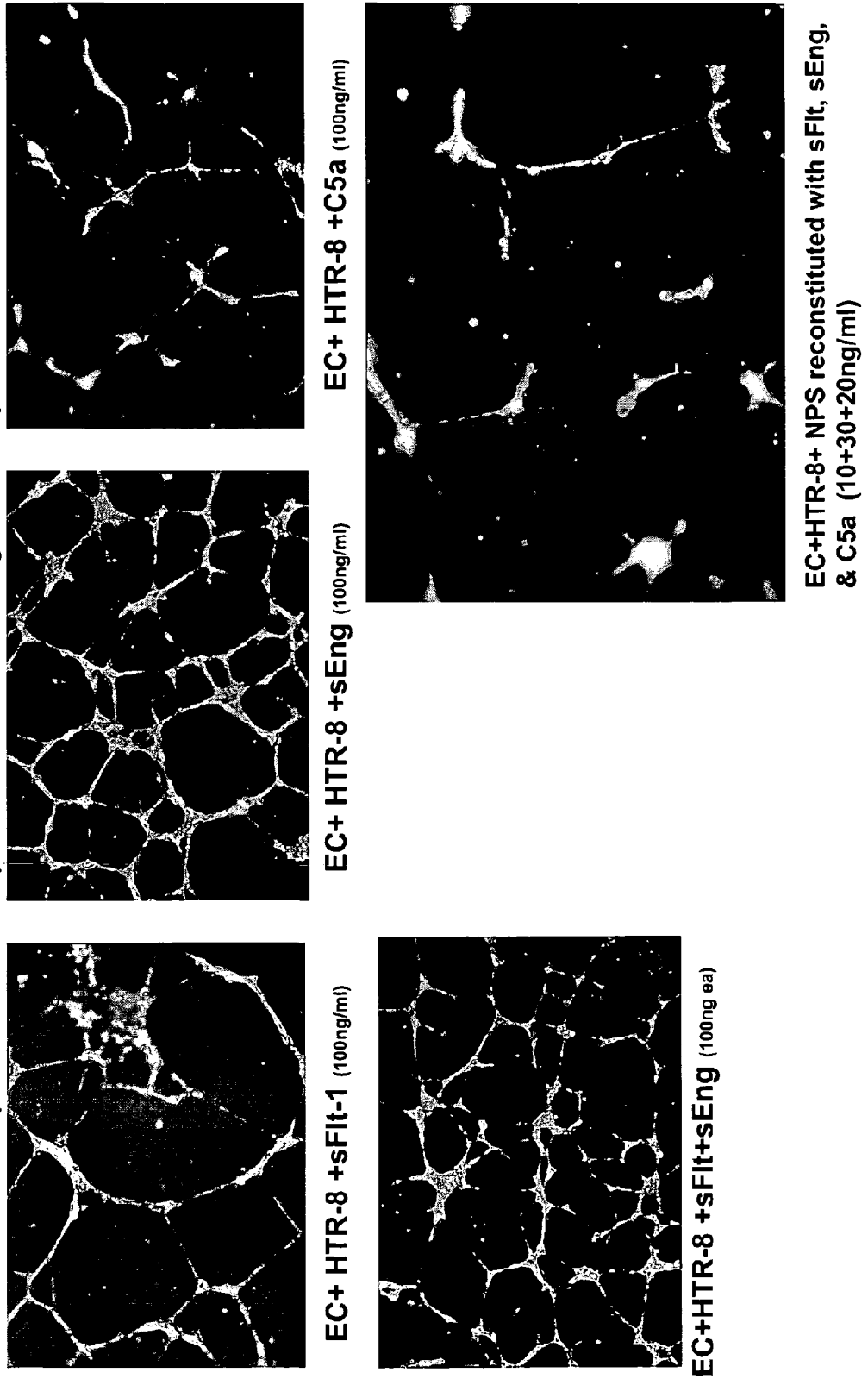
Fig 9.: Combined regulation of sFlt-1, sEng and C5a can rescue pre-eclampsia induced disrupted endothelial-trophoblast cross-talk : "Target for therapeutic intervention"

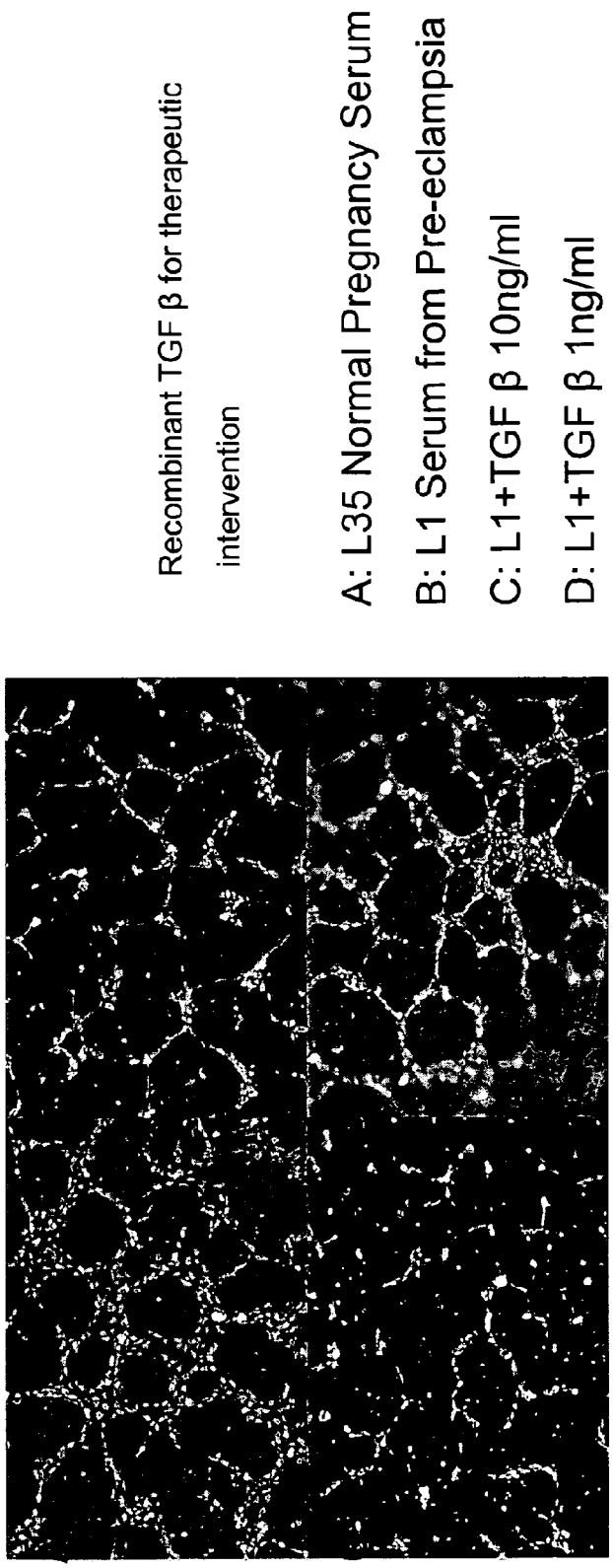
Fig 10. Low doses of TGFβ rescues pre-eclampsia serum induced disruption of capillary formation: "Therapeutic Intervention"
Recombinant TGF β for therapeutic intervention
A: L35 Normal Pregnancy Serum
B: L1 Serum from Pre-eclampsia
C: L1+TGF β 10ng/ml
D: L1+TGF β 1ng/ml

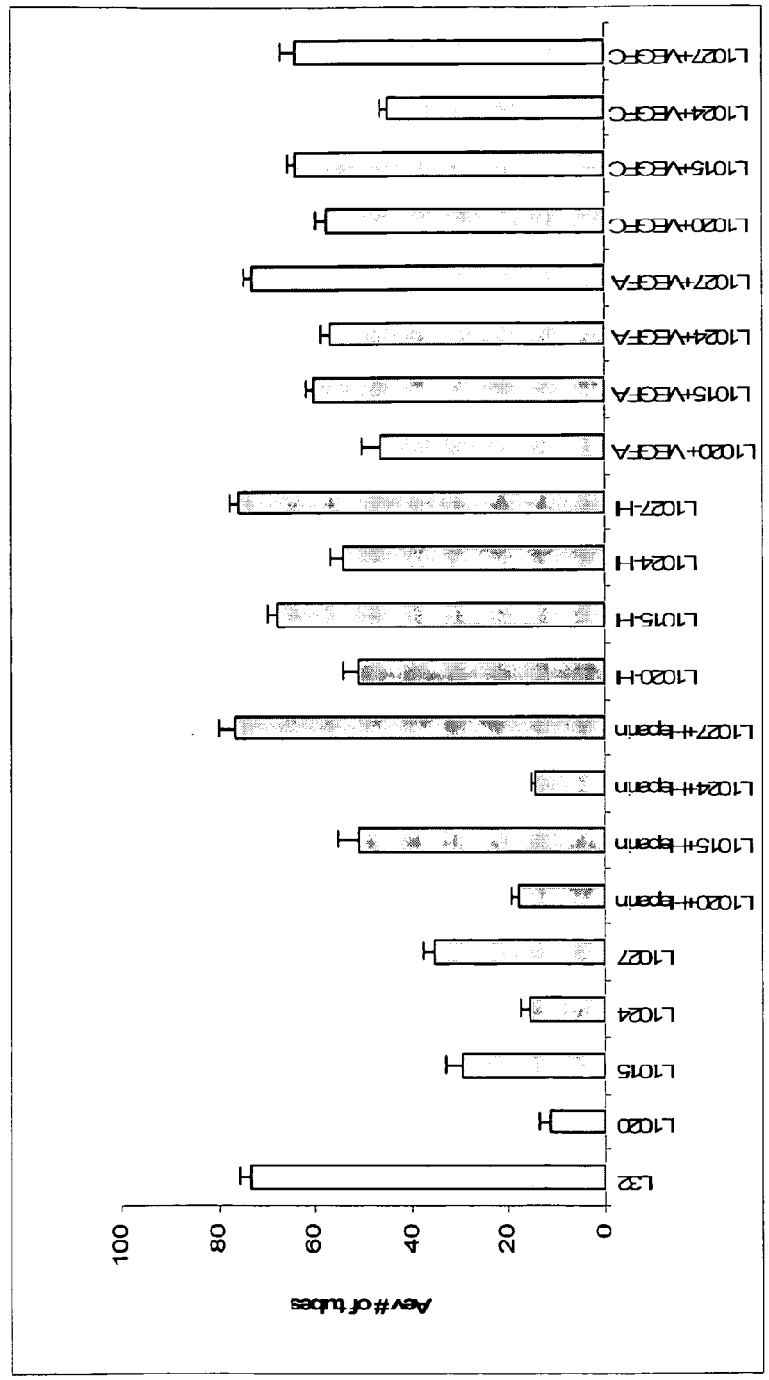

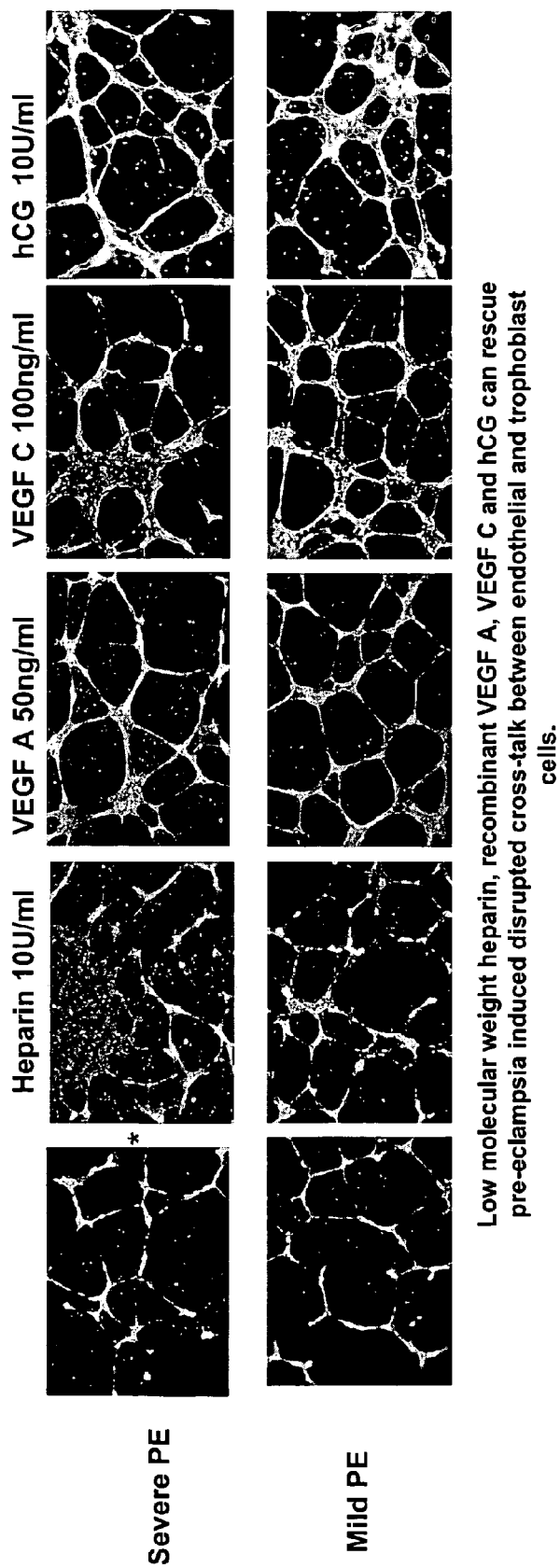
Fig 11b. Rescue of disrupted cross-talk by preeclampsia serum
Low molecular weight heparin, recombinant VEGF A, VEGF C and hCG can rescue pre-eclampsia induced disrupted cross-talk between endothelial and trophoblast cells.

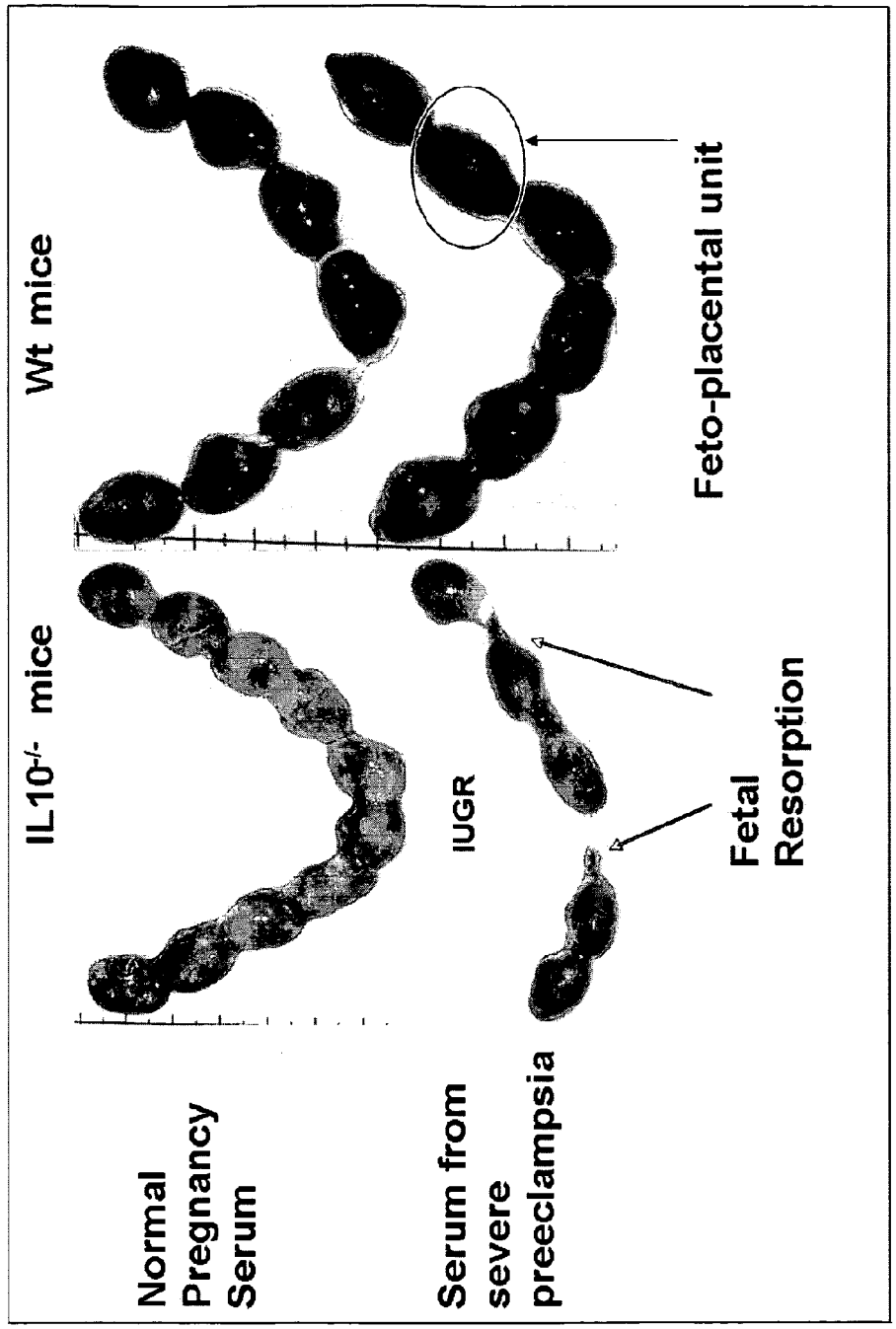
Fig 12. Effect of normal pregnancy serum and pre-eclampsia serum on pregnancy outcome (gd 17) in wild type and IL-10 null mice.

FIG. 13

TABLE 3: EFFECT OF NORMAL PREGNANCY SERUM AND PREECLAMPSIA SERUM ON BLOOD PRESSURE, PROTEINURIA, FETAL WEIGHT AND NUMBER, SYSTEMIC LEVELS OF sFlt-1 AND sEng IN IL10-/- ANIMALS.

| | sFlt-1 (ng/ml) | sEndoglin (ng/ml) | SYSTOLIC BP (mmHg) | PROTEINUREA (ug/mg) ALBUMIN/ CREATININE | AEV FETAL Wt(g) | # FETUS |
|---|---|---|---|---|---|---|
| NPS (n=9) | 61.25 ± 21.69 | 191.41 ± 45.31 | 93.46 ± 3.3 | 145.68 ± 58.96 | 1.24 ± 0.04 | 9 ± 0.81 |
| SEVERE PE SERUM (n=4) | 104.2 ± 28.7* | 385.31 ± 33.1* | 128.0 ± 12.9* | 391.89 ± 121.39* | 0.91 ± 0.12* | 8 ± 2 |
| MILD PE SERUM (n=4) | 55.29 ± 6.10 | 210.2 ± 24.2 | 113.48 ± 6.61* | 264.01 ± 94.8* | 1.23 ± 0.09 | 9 |

ALL THE VALUES ARE EXPRESSED AS MEAN +/- sd.* INDICATES STATISTICAL SIGNIFICANCE AT $P<0.05$ BY T-TEST.

FIG. 14

TABLE 4: EFFECT OF NORMAL PREGNANCY SERUM AND PREECLAMPSIA SERUM ON BLOOD PRESSURE, PROTEINURIA, FETAL WEIGHT AND NUMBER, SYSTEMIC LEVELS OF sFlt-1 AND sEng IN SYMPTOMS IN WT ANIMALS.

| | sFlt-1 (ng/ml) | sEndoglin (ng/ml) | SYSTOLIC BP (mmHg) | PROTEINUREA (ug/mg) ALBUMIN/CREATININE | AEV FETAL Wt(g) | # FETUS |
|---|---|---|---|---|---|---|
| NPS (n=8) | 68.8 + 21.6 | 176.5 + 148.4 | 102.7 + 28.1 | 387.28 + 162.9 | 1.27 + 0.09 | 8.33 + 1.5 |
| SEVERE PE SERUM (n=4) | 51.9 + 28.18 | 379.4 + 172.3* | 147.4 + 18.9* | 828.5 + 570.9* | 1.0 + 0.25 | 7.6 + 1.51 |
| MILD PE SERUM (n=4) | 75.57 + 14.3 | 200.2 + 21.2 | 101.9 + 17.58* | 228.4 + 24.2 | 1.07 + 0.1 | 8 + 0 |

ALL THE VALUES ARE EXPRESSED AS MEAN +/- sd.* INDICATES STATISTICAL SIGNIFICANCE AT $P < 0.05$ BY T-TEST.

SERUM-BASED, DIAGNOSTIC, BIOLOGICAL ASSAY TO PREDICT PREGNANCY DISORDERS

This application is a national phase application of PCT/US2009/000708, filed Feb. 4, 2009, which claims priority to U.S. Provisional Application No. 61/063,491 filed Feb. 4, 2008, the disclosures of which are incorporated herein by reference in their entirety.

BACKGROUND

Disorders of pregnancy pose a major public health problem because they involve approximately 10% of human pregnancies. Preeclampsia (PE) is one such disorder which presents itself with maternal symptoms of global endothelial disease, including glomeruloendotheliosis, liver and cerebral vascularitis. Diagnostic symptoms are high blood pressure (>140), proteinuria (>0.3 gm/ml) and general edema. (ACOG Committee on Obstetric Practice, 2002) PE is a pregnancy-specific systemic disorder characterized by a cascade of events and symptoms, including impaired trophoblast invasion, decreased placental perfusion, placental ischemia, oxidative stress and imbalance in angiogenic and prothrombotic factors which can lead to apoptosis of trophoblasts[20-23]. Studies have also shown that in preeclampsia, there are elevated levels of circulating or placental TNFα, IL-6, IL-8. IFNγ, leptin, perturbed renin angiotensin system, complement split products, antibodies to phospholipids, sFlt-1, soluble endoglin, IL2, decreased IL10, NO, hypoxia[18, 24-31] amongst host of other factors. Uteroplacental abnormalities can result in shallow placentation, poor spiral artery remodeling, and placental ischemia. PE is strictly a placental condition; it resolves after delivery. PE is diagnosed in the later half of pregnancy and the relatively late onset of clinical signs and a complex pathobiology of PE present obstacles for its study. There exist no concrete in vitro or animal models that mirror the morphological and mechanistic underpinnings of PE.

Gestational diabetes, intrauterine growth restriction, and placental abruption are other pregnancy disorders associated with placental angiogenic anomalies and ischemia. Gestational diabetes is characterized by high blood glucose levels during pregnancy. About 3%-5% of all pregnant women in the U.S. are diagnosed with the condition, which is believed to result from hormonal changes that occur during pregnancy. Increases in hormone levels made in the placenta cause insulin resistance, which increases as the placenta grows larger and produces more hormones. If the pancreas cannot produce enough insulin to overcome the effect of the increased hormones during pregnancy, sugar levels will rise, resulting in gestational diabetes.

Placental abruption affects about 9 in 1,000 pregnancies. It can occur any time after the 20th week and results from a cascade of pathophysiologic processes ultimately leading to the separation of the placenta prior to delivery. Pregnancies complicated by abruption result in increased frequency of low birth weight, preterm delivery, stillbirth, and perinatal death. [32] The causes are not well-understood; some women develop it without any identifiable cause. Known risk factors high blood pressure (140/90 mm Hg or higher), either chronic or caused by the pregnancy (either by pregnancy-induced hypertension or preeclampsia).

Intrauterine growth retardation (IUGR), defined as less than 10 percent of predicted fetal weight for gestational age, may result in significant fetal morbidity and mortality if not properly diagnosed. The condition is most commonly caused by inadequate maternal-fetal circulation, with a resultant decrease in fetal growth. Maternal causes of IUGR account for most uteroplacental cases. Chronic hypertension is the most common. Moreover, the infants of hypertensive mothers have a three-fold increase in perinatal mortality compared with infants with IUGR who are born of normotensive mothers. IURR also result from preeclampsia, which causes placental damage that result in uteroplacental insufficiency due to luminal narrowing and medial degeneration, leading to diminished blood flow to the developing infant. Consequently, the infants fail to grow normally. Treatment of the mother and the growth-restricted fetus is typically dictated by the etiology of the condition. Maternal hyperoxygenation has been evaluated in several studies and low-dose aspirin (150 mg per day) has also been studied.

Efforts have been made to provide assays for the diagnosis of PE. Numerous assays employ identification and/or measurement of various biochemical markers such as specific protein or nucleic acids in maternal samples. Exemplary are U.S. Pat. Nos. 6,735,529; 6,620,590; 6,495,330; and 6,258,540 and United States Patent Publication Nos. 2007/0185200; 2004/0038305; 2007/01785302007/0104707; 2007/0020766; and 2006/0183175. None appear to work with any consistent, reliable, degree of success. Another known assay involves culturing human trophoblasts in the presence or absence of a pregnant woman's serum or plasma and comparing viability of the cells cultured. See United States Patent Publication No. 2005/0074746. Like the biochemical marker assays, this cell-based assay is reported to be an inconsistent and unreliable predictive measure for PE.

Efforts also have been made to provide mouse strains exhibit phenotypes associated with various adverse pregnancy outcomes, including PE. Hayakawa et al. demonstrated high fetal resorption rates, hypertension, proteinuria and glomerular nephritis in pregnant BALB/C mice exposed to IL-12 stimulated splenocytes[14]. Takimoto et al. mated transgenic mice expressing components of the human renin-angiotensin system, resulting in the development of PE manifestations[15]. Similarly, mice deficient in the cyclin-dependent kinase inhibitor p57kip1 exhibit some of the features associated with PE (16). Proteinuria, hypertension, glomerulosclerosis and small liter size were also noted in spontaneously hypertensive (BPH/5) matings[17]. However, these models do not address the issue of intrinsic response in wild type animals to circulating inflammatory components and placenta-derived factors.

SUMMARY OF THE INVENTION

The invention provides a simple in vitro dual cell culture model that mimics the invasion of fetal trophoblasts over endothelial cells in response to normal pregnancy serum. The invention is based on the unexpected observation that invasive extravillous trophoblasts (EVT) from first trimester spontaneously interact with maternal endothelial cells, allowing for trophoblastic "fingerprinting" of the endothelial cell architecture, which exhibits a characteristic vacuolization, when the two cell types are co-cultured on a soluble matrix with normal pregnancy serum. In contrast, third trimester and term trophoblasts do not exhibit this vacuolization in endothelial cell co-cultures. In the absence of endothelial cells, trophoblasts themselves do not form such architecture and remain as aggregates of cells in response to growth factors from serum. Surprisingly, serum from pregnant female humans that go on to acquire complications like preeclampsia disrupts the characteristic vacuolization of the cells co-cultured. Thus, the invention is based on the premise that maternal serum is a "blueprint" that mirrors the "global welfare" of placenta and fetus. Due to trans-placental transportation, any inflammatory milieu associated with placental dysfunction would be released into circulation.

Although the invention is exemplified using preeclampsia (PE), for the reasons discussed above, the model also finds applicability in the prediction of any disorder stemming from either poor trophoblast invasion or placental ischemia, or both, including for example PE, gestational diabetes, intrauterine growth restriction (IUGR) and placental abruption. Other trophoblasitic diseases with hyper- or hypo invasive features that are similar to the foregoing can also benefit from the methods and compositions of the invention.

Accordingly, in one aspect, the invention provides an assay for assessing whether a pregnant female is at risk of developing a disorder of pregnancy associated with trophoblast invasion or placental ischemia. Exemplary disorders include preeclampsia, gestational diabetes, intrauterine growth restriction and placental abruption. The assay includes incubating a co-culture of human endothelial cells and human trophoblast cells in the presence of serum or plasma obtained from a pregnant female for a period of time sufficient to permit vacuolization (also referred to as "capillary formation" and "tube formation" in FIG. 5), and after incubation determining whether substantial vacuolization in the co-culture has occurred. By "substantial vacuolization" we mean high number of vacuoles. In this context, each vacuole is the small cavity completely bound by elongated cellular structure as indicated in FIGS. 1c and 5. As observed under microscope, vacuolization comprise of thin walled vacuoles having few branch points. The branch points are the points from which multiple vacuoles are initiated/connected. The quantity of tubes formed (also means number of vacuoles) will be substantially less by comparison with normal pregnancy serum. Normal pregnancy serum will exhibit tube-vacuole formation over about 40 tubes/well of a 48 well plate (for example between about 45 and 75 tubes/well as can be seen in FIGS. 7c and 11a). This average number of such tubes-vacuoles in response to normal pregnancy serum is defined as "normal endothelial-trophoblast cross-talk". In contrast, serum or plasma from a pregnant female at risk for or having preeclampsia will exhibit tube-vacuole formation substantially less than about 40 tubes per well (for example between about 5 and 35 tubes/well as can be seen in FIGS. 7c and 11a). This average number of such tubes-vacuoles is defined as "abnormal endothelial-trophoblast cross-talk".

Optionally, an addition co-culture in the absence of serum from a pregnant female can be performed under the same conditions and the two co-cultures compared to determine whether vacuolization in the first co-culture has occurred. Typical incubation time is between 10 and 12 hours, in carbon dioxide at 37° C. and preferably the serum, in an amount ranging from 0.5 to ml will have been taken from the first trimester of the pregnant female's pregnancy. The assay can be performed on a natural or synthetic soluble matrix. Exemplary matrices include matrigel, collagen, fibronectin, elastin and combinations thereof.

The human endothelial cells employed may be from umbilical vein or they may be uterine, myometrial, cedicual, aorta, microvascular, dermal or other endothelial cells that express VE-cadherin, PECAM, and/or Aquaporin 1. The trophoblasts employed may be from primary villous or extravillous trophoblasts, HTR8, 3A or JEG3 trophoblasts or other invasive trophoblasts isolated from choriocarcinomas.

This simple assay, based on "cross-talk" between fetal and maternal cells at the fetal-maternal interface can be used as diagnostic tool to predict pregnancy outcomes as early as 7-10 weeks of pregnancy and impending pregnancy complications like preeclampsia, intrauterine growth restriction, gestational diabetes and placental abruption. The method is simple, non-invasive, cost effective, and can be completed within about 8-12 hrs. It requires a one time draw of blood (1-5 ml) at different stages of pregnancy, preferably between 7-21 weeks, so as to yield serum of about 0.3-5 ml, preferably about 0.5-2 ml for the experiment. The method does not require any major equipment and can be carried out by any diagnostic lab. This method is unique to pregnancy, due to the fact that EVT that are used here are the fundamental cells appearing only during the window of pregnancy.

In another aspect, the invention includes a kit for assessing whether a pregnant female is at risk of developing a disorder of pregnancy associated with trophoblast invasion or placental ischemia. The kit includes a natural or synthetic soluble matrix. Exemplary matrices include matrigel, collagen, fibronectin, elastin and combinations thereof. Also included in the kit are labeled human endothelial cells and labeled human trophoblast cells. The human endothelial cells employed may be from umbilical vein or they may be uterine, myometrial, cedicual, aorta, microvascular, dermal or other endothelial cells that express VE-cadherin, PECAM, and/or Aquaporin 1. The trophoblasts employed may be from primary villous or extravillous trophoblasts, HTR8, 3A or JEG3 trophoblasts or other invasive trophoblasts isolated from choriocarcinomas. In using the kit, serum from the pregnant female patient is drawn. The endothelial cells and the trophoblast cells are co-cultured on the matrix and the appropriate amount (see above) of the serum is added. The culture is incubated for at least about 8 hours and the results observed.

In yet another aspect, the assay of the invention is amenable to high-throughput screening, either for the identification of compounds or substances (i.e., agents) useful in the treatment of the aforementioned pregnancy disorders or conditions or useful as contraceptives or abortificients. This can be achieved by modification of published methods, for example, see Withington.[33] Briefly, labeled endothelial cells and labeled trophoblasts are plated on an appropriate matrix. The cells are stimulated with preeclampsia serum (to identify compounds or substance to treat pregnancy disorders) in the presence or absence of the test compound or substance, and incubated for an appropriate period of time, typically 12 to 14 hours, under appropriate incubation conditions. After incubation, the cells are observed and analyzed to determine whether the test compound or substance has stimulated the duel cell cross-talk between the endothelial cells and the trophoblasts as compared to the control. PES is expected to disrupt the cross-talk between endothelial cell and trophoblasts while potential therapeutics that can reverse this disruption will be beneficial in the treatment of the aforementioned disorders or conditions. Duel cell cross-talk can be quantified based on the ratio of the two florescence signals. To identify agents useful as contraceptives or abortificients, the same method described above may be employed with one modification: in this screen normal pregnancy serum is employed instead of preeclampsia serum for stimulation. Normal pregnancy serum is expected to support the cross-talk between endothelial cells and trophoblasts while compounds or substances that disrupt this architectural imprinting will be useful as contraceptives or abortificients.

In yet another aspect, the invention provides a humanized in vivo animal model using interleukin-10 (IL10) null animals that was found to be highly sensitive to predict clinical symptoms of preeclampsia like proteinuria, elevated blood pressure and kidney pathology, using a single injection of serum from pregnancy. The term "humanized" as used herein refers to the mimicking of the onset of human conditions in the animal using human material. In the present case, administration of human serum samples induced preeclampsia like symptoms in pregnant IL 1-0 null mice; however other rodents, including guinea pigs and hamsters may be employed as long as they are deficient in IL 10 expression. This model can be used for high throughput screening for the discovery of molecules that can restore the serum-induced disrupted cross-talk and alleviate preeclampsia and/or other disorders of placental ischemia. Such examples include but not limited to recombinant human proteins and amino acids like rH VEGF A, rH VEGF C, hCG, TGF Beta, low molecular weight heparin and other small synthetic, semi-synthetic or natural molecules. Administration of potential cross-talk restoring agents to an animal that has previously been administered human PE serum and is exhibiting PE-associated symptoms, and observing whether the PE-associated symptoms are alleviated thereby provides a method for screening for agents to treat PE and/or other disorders of placental ischemia.

In developing the assay of the invention, it was observed that complement split C5a levels are elevated in pre-eclampsia two-fold above the normal values seen in pregnancy. Further, data showed that the onset of preeclampsia appears to be related to the levels of C5a. We also discovered, unexpectedly, that such elevated C5a levels are detrimental to the proactive cross-talk between trophoblasts and endothelial cells inhibiting the vacuolization, which in clinical settings can lead to reduced trophoblast invasion of spiral arteries (see FIG. 9). In combination with elevated sFlt-1 and soluble endoglin, elevation of C5a was found to synergistically become functionally lethal to trophoblast-endothelial cross talk at the fetal-maternal interface (FIG. 9). Thus, controlling increases in maternal C5a levels is a therapeutic method in the treatment of pregnancy disorders such as preeclampsia. Furthermore, modulators of maternal C5a levels are suitable compositions for therapeutic intervention for preeclampsia and other disorders of poor trophoblast invasion resulting in placental ischemia. Examples of such modulators include peptides, N-acetylated macrocyclic peptide 3D53, cyclic peptide derivatives and other C5a antagonists[34].

Similarly, other proteins expressed on the trophoblasts or endothelial cells or both are required for normal cross-talk and architectural imprinting of trophoblasts on endothelial cells. Such proteins are exemplified by aquaporins (e.g. aquaporin-1), Delta like ligand (e.g. DLL4), whose function, when blocked using specific monoclonal antibodies, was found to disrupt cross-talk between endothelial cells or trophoblasts. Since preeclampsia is trophoblastic disease with shallow trophoblast invasion, such proteins are targets amenable to therapeutic manipulations so as to facilitate complete and optimal trophoblast invasion leading to normal pregnancy. Molecules that can modulate these targets can be screened based on the described method and used to treat disorders of placental ischemia resulting from poor trophoblast invasion such as preeclampsia, gestational diabetes, intrauterine growth restriction and placental abruption.

DESCRIPTION OF THE DRAWINGS

FIG. 1 is a photographic representation of the effect of normal pregnancy serum at 37-40 weeks on endothelial cells as described in Example 1. FIG. 1a shows the endothelial cells as a monolayer on a two dimensional culture, FIG. 1b shows endothelial cell architecture on a three dimensional basement matrix-matrigel and FIG. 1c shows the kinetics for the architectural rearrangement for endothelial cells.

FIG. 2 is a photographic representation of the effect of normal pregnancy serum on trophoblast cells as described in Example 2.

FIG. 3 is a photographic representation showing that NPS supports a trimester-specific differential interaction between trophoblasts and endothelial cells as described in Example 3.

FIG. 4 is a photographic representation showing the results of Example 4 demonstrating that preeclampsia serum disrupts the interaction of trophoblasts and endothelial cells. Large vacuoles and substantially smaller branch points can clearly be seen FIG. 5 is a photographic and a graphic representation of the results of the experiment described in Example 4 showing the quantitative effect of NPS, mild PE and severe PE on first trimester trophoblast-endothelial cell co-cultures.

FIG. 6 is a graphic representation of the results of the cytotoxicity assay described in Example 5.

FIG. 7 is a photographic and a graphic representation of the results of the longitudinal studies of endothelial-trophoblast co-cultures described in Example 6.

FIG. 8A is a photographic representation of the results of endothelial cells and HTRB trophoblasts co-cultured and stimulated with pregnancy serum with or without recombinant human complement split product C5a, as described in Example 7.

FIG. 8B is a table showing complement split product C5a levels are elevated on serum samples from preeclampsia.

FIG. 9 is a photographic representation of the results of endothelial cells and HTR8 trophoblasts co-cultured and stimulated with normal pregnancy serum with or without sFlt-1, sEng, or C5a, as described in Example 7.

FIG. 10 is a photographic representation of the results of endothelial cells and HTR8 trophoblasts co-cultured and stimulated with normal pregnancy serum or severe PE serum with or without TGFβ as described in Example 8.

FIG. 11 is a graphic representation and a photographic representation of the results of the experiment described in Example 9 in which PE serum induced disrupted vacuolization is reversed by addition of certain hormones and growth factors.

FIG. 12 is a photographic representation of the results of the administration of normal pregnancy serum and preeclampsia serum on pregnancy outcome (gestational day 17) in wild type and IL-10 null mice as described in Example 10.

FIG. 13 is a table showing the effect of normal pregnancy serum and preeclampsia serum on blood pressure, proteinuria, fetal weight and number, systemic levels of sF1t-1 and sEnq in IL10 animals.

FIG. 14 is a table showing the effect of normal pregnancy serum and preeclampsia serum on blood pressure, proteinuria, fetal weight and number, systemic levels of sF1t-1 and sEnq in symptoms in WT animals.

DETAILED DESCRIPTION

Mammalian reproduction involves a complex, highly choreographed set of molecular processes that include interactions between the hormonally stimulated uterus and the developing blastocyst, implantation, a period of placental and fetal development, and a terminal pathway composed of decidual/membrane activation, myometrial contractility, and cervical ripening[1-3]. While metabolic changes and the placental microenvironment are programmed in a pregnancy compatible manner, pregnancy presents itself as an immunological and hormonal paradox[4]. The role of estrogen and progesterone is well known in uterine receptivity, implantation, local immune modulation, and early pregnancy success[2]. Insulin resistance similar to that imparted by inflammatory responses in non-pregnant individuals is exhibited during pregnancy[5], which leads to the sustained transplacental nutrient flux required for fetal growth and development. Trophoblast invasion of the decidua is considered central to the free flow of nutrients and blood to the fetus. A poor perfusion of placenta, defective trophoblast invasion and remodeling of spiral arteries, and ensuing placental ischemia have been thought to be associated with intrauterine growth restriction (IUGR) and preeclampsia (PE).

Initial evidence supported the hypothesis that alterations in endothelial function were responsible for the pathophysiology of PE[5, 10]. However, reassessment of the disorder has led to a new theory involving the placenta and secondary maternal illness of hypertension, proteinuria and edema (5). PE remains highly heterogeneous and dangerous late pregnancy complication. A key factor appears to be that the disease is a pregnancy and placenta-specific syndrome. Although endothelial dysfunction is a major change, it appears to be a consequence of the interaction between poor placental perfusion and maternal factors resulting in systemic inflammatory syndrome[5, 10]. As a matter fact, normal pregnancy is also associated with somewhat elevated inflammatory responses such as insulin resistance, leptin production and apoptotic or necrotic trophoblast debris in circulation (11). Thus, one hypothesis is that PE is an extreme manifestation of mild inflammatory conditions typical of normal pregnancy. These observations suggest that PE may also represent an imbalance between inflammatory and anti-inflammatory milieu during pregnancy.

To establish a link between preeclampsia, placenta-endothelial dysfunction, and systemic inflammatory syndrome, it is tempting to hypothesize that the factors that choreograph co-onset of local defects at the maternal fetal interface and systemic manifestation of PE-associated symptoms are present in patient's circulation. This implies that serum from PE patients and normal pregnancy subjects could provide a "blueprint" of etiologic factors. The maternal factor should originate in the placenta, must be disseminated to circulation, and be highly elevated during gestation because it disappears after the delivery of the placenta. Although in vitro studies suggest that serum from a sub group of PE patients causes apoptosis in trophoblast cells due to activation of complement cascade (our unpublished data), an appropriate animal model should allow for its in vivo evaluation and for identification of the exact nature of the placenta derived maternal factor(s) in vitro.

The choice of animal model for experimental studies of adverse pregnancy outcome in response to environmental factors is limited because of high variability in the reproduction biology of mammalian species (12). The requirement for a closely related animal is particularly important because, where possible, identical phenotypic and molecular biomarkers should be monitored in both human and animal models. These requirements plus the availability of immunological, hormonal, and molecular reagents limit the choice of a model of mice. The similarities between human and mouse pregnancy begins with the hormonal regulation of uterine receptivity for blastocyst implantation[2]. This is followed by hemochorial placentation, recruitment of phenotypically and functionally similar immune cells, placental production of cytokines, chemokines and hormones, and spiral artery remodeling by invading trophoblasts. We have recently used wild type and knockout strains of mice to study the immunobiology of pregnancy in response to inflammatory agents and cytokine deficiency (13). Such studies provide important information on biological assays and molecular targets relevant to human studies.

Since local and systemic features of PE are inter-dependent, serum from pregnancy can provide a "blueprint" of PE pathology and mimic clinical symptoms associated with PE, specifically, elevated blood pressure, proteinuria, kidney pathology, and IUGR, in an appropriate animal model. A small number of experimental models have included mouse strains that are either genetically modified in growth or angiotensinogen regulatory pathways, or administered with treated leukocytes, but do not address the issue of intrinsic defects or local/systemic inflammation[14-17]. In our model, a single in vivo administration of serum from PE patients is employed in pregnant, wild-type mice without a predisposed condition. Importantly, this serum-based model is pregnancy specific, as PE serum does not cause any ill effects such as elevated blood pressure and proteinuria in non-pregnant animals The observed vascular deficiency in PE reflects a defective cross-talk between invading trophoblasts and the spiral artery endothelium resulting in poor spiral artery remodeling and free flow of nutrients to the fetus. Because of co-onset of local placental anomalies and systemic maternal condition, we hypothesize that serum from PE patients can provide a "blueprint" of causative factors. We further propose that a mouse model and an in vitro model of endothelial cell-directed fingerprinting of trophoblasts mimicking spiral artery remodeling can be established to unravel the intrinsic ability of serum to induce in vivo or in vitro hallmark PE-associated characteristics.

Normal pregnancy involves the close interaction between placental cells and maternal cells led by migration of trophoblasts into the maternal tissue. Pregnancy specific complications like preeclampsia, is characterized by shallow trophoblast invasion of the maternal spiral arteries. Trophoblasts are pregnancy specific stem cells representing fetus, while the endothelial cells represents the functional cells of maternal spiral arteries. Serum represents a unique media that hosts numerous bio-markers that mirrors the global welfare of fetus and mother in successful pregnancy. Thus, serum can "blueprint" any anomalies very early during the pregnancy, much before clinical diagnosis of the onset of complications.

The following examples illustrate certain exemplary aspects and embodiments of the invention and are included for illustration purposes.

EXAMPLE 1

Effect of Normal Pregnancy Serum (NPS, 37-40 weeks) on Endothelial Cells

Human umbilical cord endothelial cells (HUVEC) and human uterine endothelial cells (HUtEC) were obtained from Cambrex (East Rutherford, N.J., USA). Growth factor-reduced Matrigel representing basement membrane (BD Biosciences, San Diego, Calif., USA) was thawed overnight at 4° C. and mixed to homogeneity. The 48-well culture plates (Costar) were coated with 0.1 ml of Matrigel and allowed to gelatinize at 37° C. for 30 min. $2.5 \times 10^4$ endothelial cells (HUtEC or HUVEC) labeled with cell tracker orange CMTMR (Molecular Probes, Eugene, Oreg.) were plated (1:1) in the presence of RPMI media containing 10% human pregnancy serum on the matrigel-coated plates. The architectural and morphological changes that took place were monitored and recorded 12-14 hrs after incubation under standard culture conditions using florescence microscopy (4× magnifications, Nikon Eclipse TS 100 coupled with CCD camera;

photographs take every two hours). The endothelial cells migrated, underwent cytoskeletal reorganization, and formed tube-like capillary structures impregnated with vacuoles and branch points where they assume structures similar to their in vivo morphology. See FIG. 1c. The numbers of completely formed vacuole were recorded manually as number of tubes in four different fields of view and defined as vacuolization. An average of 45±6 vacuoles/well of a 48 well plate are formed. FIG. 1a shows the endothelial cells as a monolayer on a two dimensional culture and FIG. 1b shows endothelial cell architecture on a three dimensional basement matrix-matrigel. FIG. 1a-c are copies of photographs taken at t=12 hours.

EXAMPLE 2

Effect of Normal Pregnancy Serum on Trophoblast Cells

The first trimester human trophoblast cell line HTR8 (representing normal invasive extravillous trophoblasts), the third trimester human trophoblast cell line TCl-1, and the first trimester human villous trophoblast cell line 3A were used in the following studies. Human HTR-8 cells and TCl-1 cells were a gift from Dr. Charles Graham (Queens University, Canada) and human 3A cells r were a gift from Dr. Gil Mor, Yale University, USA.

Cytotrophoblasts from human placental tissue were isolated according to published methods. Briefly, placental tissues were digested with decreasing concentrations of trypsin-DNase 1 (trypsin, 1 mg/ml; and DNase, 1.5 mg/ml) at least four times at 37° C. for 20 min each. The cells from the first digestion were excluded. The cell mass collected in the following steps was treated with a lysis buffer (0.15 M $NH_4Cl$, 1 mM $KHCO_3$, and 0.1 mM EDTA (pH 7.3) for 5 min at room temperature with constant shaking to lyse the red blood cells (RBCs), which if not removed disturb separation on Percoll gradients. Cytotrophoblasts isolated in this manner were stained for cytokeratins or CD45 (a marker for immunocytes) to ascertain their purity (>95%).

Both freshly isolated primary trophoblasts (isolated as described above and cultured overnight) and trophoblast cell lines HTR8, TCl-1 and 3A were maintained in Roswell Park Memorial Institute (RPMI) 1640 media purchased from Gibco (Gaithersburg, Md., USA) supplemented with 10% fetal bovine serum, 2 mM L-glutamine (Gibco BRL), 100 U/ml penicillin (Gibco BRL) and 0.1 mg/ml streptomycin (Gibco BRL). Cell lines were grown to ~80% confluence and less than eight passages were used in the study. HUVEC and HUtEC cells were maintained in EBM-2 and used within six passages. All cells were maintained in standard culture conditions of 5% $CO_2$ at 37° C.

$2.5 \times 10^4$ trophoblast cells in different trimesters, labeled with cell tracker green CMFDA (Molecular Probes, Eugene, Oreg.), were plated on Matrigel-coated plates and stimulated with media containing 10% NPS as described in Example 1. The architectural and morphological changes that took place were recorded 12-14 hrs after incubation under standard culture conditions using florescence microscopy (4× magnifications, Nikon Eclipse TS 100 coupled with CCD camera; photographs take every two hours). None of the trophoblast cells formed capillary tube like structures on matrigel in response to stimulation with NPS, reflecting their inherent behavior in vivo. These results are shown in FIG. 2, which is a reproduction of a photograph taken at the end of the experiment.

EXAMPLE 3

NPS Supports Trimester-Specific Differential Interaction with Endothelial Cells $2.5 \times 10^4$ endothelial cells labeled red and trophoblasts from human subjects, each from different trimesters labeled green, were co-cultured on matrigel-coated plates and stimulated with Normal Pregnancy Serum (NPS) (sample L31, see Table 1) as described in Examples 1 and 2. Gestational age specific architectural patterns were observed. As seen in FIG. 3, left panel (which is labeled "EC+HTR8+L31"), surprisingly only the first trimester HTR8 trophoblasts spontaneously interact and align with endothelial cell architecture. S3A cells, representing villous trophoblasts from first trimester, attract endothelial cells and form massive branch points that allow reduced vacuolization only around its vicinity. (See FIG. 3, middle panel, labeled "EC+3A+L31.") In contrast, term trophoblasts and third trimester TCL-1 trophoblasts tend to naturally impede the capillary formation by endothelial cells. Smaller vacuoles result. (See FIG. 3, right panel labeled "EC+TCL-1+L31.") Thus, NPS supports the proactive cross-architectural realignment of endothelial and first trimester trophoblast cells, but does not support realignment of the cells in the third trimester and at term.

EXAMPLE 4

Preeclampsia Serum Disrupts Gestational Age-Specific Differential Interaction with Endothelial Cells Blood samples were obtained from normal pregnant human subjects and preeclamptic human subjects during first (6-12 weeks), second (13-20 weeks) or third (21-40 weeks) trimester of pregnancy and serum separated routinely. Pregnancies were considered normal when there were no medical complications. Preeclampsia was defined when blood pressure was >140/90 mm Hg at least on two occasion 4 hours to 1 week apart and with proteinuria >300 milligram in 24 hr urine collection. Exclusion criteria were chronic hypertension, diabetes, antiphospholipid antibody syndrome, thrombophillic anomalies, antepartum and postpartum complications. All the studies were approved by the human institutional review board at the Women and Infants Hospital of Rhode Island. The samples were analyzed for content of sFlt-1, sEng, C5a and hCG levels using commercially available respective ELISA kits according to manufacturers protocol. The profiles of representative samples are provided in Table 1.

TABLE 1

Profiles of representative human pregnancy serum samples indicating gestational week of collection, onset of disease and severity of disease.

| Number | Preeclampsia/ Normal | Gestational Week | Onset | Severity |
| --- | --- | --- | --- | --- |
| L32 | Normal | | | |
| L31 | Normal | | | |
| L45 | Normal | | | |
| L1045 | Normal | 39 | | |
| L1037 | Normal | 35 | | |
| L1051 | Normal | 40 | | |
| L12 | Preeclampsia | 35 | | |
| L1015 | Preeclampsia | 38 | late | severe |
| L1035 | Preeclampsia | 42 | late | moderate |

TABLE 1-continued

Profiles of representative human pregnancy serum samples indicating gestational week of collection, onset of disease and severity of disease.

| Number | Preeclampsia/ Normal | Gestational Week | Onset | Severity |
|---|---|---|---|---|
| L1048 | Preeclampsia | 33 | early | severe |
| L1 | Preeclampsia | 34 | early | severe |
| L1020 | Preeclampsia | 36 | late | severe |
| L1027 | Preeclampsia | 40 | late | moderate |
| L35 | Normal | | | |
| L1024 | Preeclampsia | 41 | late | moderate |
| P118 | Normal | | | |
| PS318 | Preeclampsia | 7 | | severe |
| PS299 | Preeclampsia | 27 | | mild |
| PS303 | Preeclampsia | 14 | | severe |
| PS334 | Preeclampsia | 26 | | mild |
| Pre13 | Preeclampsia | 36 | | mild |

$2.5 \times 10^4$ endothelial cells labeled red and $2.5 \times 10^4$ trophoblasts, each from different trimesters labeled green, were co-cultured on matrigel coated plates and stimulated with either NPS or mild or severe PE serum (PES refers to Preeclampsia Serum) as described in previous examples for NPS alone. Exemplary results are shown in FIG. 5. Serum from either mild (sample L1035; middle left panel) or severe (sample L1; bottom left panel) preeclampsia patients blocks the "cross-talk" between endothelial-trophoblast cells, causing obvious differences in architecture as compared to the same cells stimulated under the same conditions with NPS serum (sample L31; top left panel). Preeclampsia can be classified as mild or severe. Severe preeclampsia is characterized by (1) a systolic blood pressure greater than 160 mm Hg or diastolic blood pressure greater than 110 mm Hg on 2 occasions at least 6 hours apart in a woman on bed rest and (2) the presence of significant proteinuria. Marked proteinuria is defined as 5 g or more of protein in a 24-hour urine collection. Severe preeclampsia, at times, may be associated with oliguria, cerebral or visual disturbances, pulmonary edema or cyanosis, epigastric or right upper quadrant abdominal pain, impaired liver function, and thrombocytopenia. In mild preeclampsia (or moderate PE), hypertension and proteinuria are present, but not to these extreme levels, and the patient has no evidence of other organ dysfunction. (see http://www.e-medicine.com/med/topic1905.htm Preeclampsia (Toxemia of Pregnancy)).

The number of vacuoles (or tubes) formed per sample were counted. Exemplary results are shown in the graphic panel on the right. As compared to the control serum free media (SFM) and NPS, the cells co-cultured with either mild or severe PE serum exhibited significant decreases in capillary tubes formation (63 versus 35 and 26). Statistical significance of experimental differences was assessed using Student's paired t-test. The differences were considered to be statistically significant when the p value was <0.05.

EXAMPLE 5

Cytotoxicity Assay

Since disruption of tube/vacuole formation could have been due to cell death induced by toxic components present in the human serum, a cytotoxicity assay was performed as follows. Growth factor-reduced Matrigel (representing basement membrane) was obtained (BD Biosciences, San Diego, Calif., USA), thawed overnight at 4° C., and mixed to homogeneity. 48-well culture plates (Costar) were coated with 0.1 ml Matrigel and allowed to gelatinize at 37° C. for 30 min. HTR8 trophoblasts or endothelial cells ($2.5 \times 10^4$) were plated (1:1) in the presence of serum free media containing 10% human normal pregnancy serum (NPS) severe preeclampsia serum (PES) or mild preeclampsia serum (mPE). After overnight incubation, the cells were isolated from the Matrigel using BD cell recovery solution (BD Biosciences, USA), stained with propidium iodide (PI) solution (0.1%), and analyzed by flow cytometry. Live cells do not take up PI while dead cells are stained by red color florescence that can be quantified and expressed as % PI positive (dead) cells by FACS (BD Canto, BD Biosciences, USA). The results expressed as percentage of dead cells as indicated by the number of cells that have taken up propidium iodide stain (PI) out of total cell population and are illustrated in FIG. 6. Both the normal pregnancy serum (NPS) and the serum from mild and severe preeclamptic human female patients exhibited substantially low percentages of dead cells (about 15%) than normal, and is comparable to RPMI media without the presence of serum (Serum-free Media SFM). Neither the endothelial cells nor HTR8 cells were killed by the preeclampsia serum samples. Thus, the disruption of the characteristic architecture formed by the endothelial cells and HTR8 trophoblasts is not due to cell death.

EXAMPLE 6

Quantitative Effect of NPS, Mild PE and Severe PE on First Trimester Trophoblast-Endothelial Cell Co-Cultures Longitudinal studies with PE serum on endothelial-trophoblast co-cultures were next undertaken. $2.5 \times 10^4$ endothelial cells and $2.5 \times 10^4$ HTR8 trophoblast cells were co-cultured on matrigel, stimulated with human PE serum collected at different weeks of pregnancy and incubated 12-14 hours. The number of vacuoles/tubes formed and signature pattern of architectural morphology were recorded. FIGS. 7a and 7b represent the signature architectural morphology of the co-cultures whose photographs were taken at the end of the incubation (12-14 hrs) in response to serum samples collected at different stages of pregnancy (see Table 1 for the descriptions of type of serum (mild or severe PE or NPS) used). Left and right panels represent photographs (duplicate) taken from two different field of view of a well. The number of vacuoles (or tubes) formed per sample were counted and the results are shown in FIG. 7c in which, the week of blood draw and pregnancy outcome is also indicated below the boxed graphic. The results illustrated in these figures demonstrate that preeclampsia serum disrupts the characteristic "architectural imprinting" of HTR8 and endothelial cells as early as 7-14 weeks of pregnancy and can therefore be used as an early predictive tool to assess likelihood of a patient developing preeclampsia. Statistical significance of experimental differences was assessed using Student's paired t-test. The differences were considered to be statistically significant when the p value was <0.05.

EXAMPLE 7

Serum Factors from PE that Contribute to Abnormal Endo-Tropho Cross-Talk: Synergistic Effects of Complement Split Product C5a with Soluble Factors Previous studies (reference 18 and cross references therein) indicate that PE is associated with elevated levels of the soluble form of Flt-1 (sFlt-1), also known as soluble vascular endothelial growth factor R1 (VEGF R1). sFlt-1 is an alternate splice variant of VEGF R1, which exhibits high affinity for growth factors like VEGF and placental growth factor (PlGF) and binds to these proteins, blocking their functional activities. Similarly, endoglin (also known as CD105) is a co-receptor for transforming growth factor beta (TGFβ). Soluble forms of endoglin (sEng) bind TGFβ and impair its signaling. Surprisingly, exogenous spiking of sFlt-1 or sEng at levels present in normal pregnancy serum or in preeclampsia serum fails to disrupt the cross-talk between trophoblasts and endothelial cells. For this reason, we expected that PE serum would affect the vacuolization of endothelia-trophoblasts irrespective of sFlt-1 or endoglin levels. Given the possibility that these soluble factors are not the cause but consequence of an upstream factor, we next analyzed levels of sFlt-1, sEng, and complement split product C5a in the normal, severe, and mild pregnancy serum samples set forth in Table 1 (see Example 4). As shown in Table 2, severe PE serum shows a statistically significant elevation of C5a, sFlt-1, and sEng levels that reflects at both early and late onset of the disease.

TABLE 2

Complement split products C5a are elevated in serum samples from preeclampsia.

| | sEng (ng/ml) | sFlt-1 (ng/ml) | C5a (ng/ml) |
|---|---|---|---|
| Normal (n = 25) | 16.93 ± 18.17 | 4.4 + 4.33 | 29.77 + 29.19 |
| Mixed PE Population (n = 37) | 45.88 ± 41.38** | 21.43 + 11.6** | 53.44 + 37.73[a] |
| Severe (n = 11) | 56.68 ± 38.26** | 26.89 + 11.92** | 57.94 + 30.14[b] |
| Mild (n = 26) | 41.38 ± 42.57[a] | 19.15 + 10.91** | 51.57 + 40.92 |
| Early Onset (n = 9) | 67.56 ± 45.00[a] | 25.57 + 14.76** | 48.91 + 22.53[c] |
| Late Onset (n = 28) | 39.21 ± 37.94[a] | 20.15 + 10.26** | 54.84 + 40.77[a] |

All values are expressed as mean +/− sd.
**, [a], [b], [c] indicates statistical significance at $P < 0.001$, $P < 0.01$, $P < 0.02$, $P < 0.07$.
Parenthesis indicates the number of serum samples analyzed.

As indicated in Table 2, the values of sFlt-1, sEng, and C5a are statistically much higher in preeclampsia serum compared to normal pregnancy serum, irrespective of disease phenotype. Importantly, sFlt-1 and sEng levels are substantially lower in mild as compared to severe preeclampsia. We sought to explore the effect of C5a on endothelial-trophoblast cross-talk experimentally as described below.

Briefly, $2.5 \times 10^4$ labeled endothelial cells and $2.5 \times 10^4$ HTR8 trophoblasts were co-cultured on matrigel coated plates, stimulated with normal human pregnancy serum with or without 100 ng/ml recombinant human complement split product C5a, and incubated for 12-14 hours as described in previous examples. The signature patterns of architectural morphology were recorded. Exemplary results are shown in FIG. 8 for sample L35. NPS spiked C5a disrupts the endothelial-trophoblast cross-talk (panel "B"), indicating that imbalance in complement cascade split products could be one of the causes for the loss of activity. Further, to assess the complementary role of C5a to the presence of sFlt-1 and sEng, the following experiment was carried out.

Labeled endothelial cells and HTR8 trophoblasts ($2.5 \times 10^4$ each) were co-cultured on matrigel and stimulated with normal pregnancy serum with or without sFlt-1, sEng, or C5a as described earlier. Exemplary results are shown in FIG. 9, which shown that NPS spiked with sFlt-1, sEng and C5a, in combinations, at physiologically relevant amounts can cause more dramatic and synergistic disruption of "endo-tropho cross-talk" and vacuolization of endothelial/HTR8 cell co-cultures than each of them independently. This also demonstrates that the "cross-talk" between endothelial cells and trophoblasts cannot be disrupted by spiking NPS with exogenous soluble Flt-1 or soluble Eng at concentrations seen in either severe or mild pre-eclamptic serum unless there is elevated C5a levels that acts as catalyst to disrupt the cross talk.

Thus, these results provide direct evidence that C5a is possible target amenable to pharmacological manipulations by which discovery of therapeutic interventions can be sought.

EXAMPLE 8

Low Dose TGFβ Rescues Preeclampsia Serum Induced Disruption of Capillary Formation $2.5 \times 10^4$ endothelial cells and $2.5 \times 10^4$ HTR8 trophoblasts were co-cultured 12-14 hours on matrigel and stimulated with normal pregnancy serum (NPS) or severe PE serum (PES) with or without TGFβ. Exemplary results for samples L35 and L1 are shown in FIG. 10. As the pictorial representations labeled A-D indicate, NPS support the vacuolization of trophoblasts and endothelial cells and PES disrupts this cross talk. Our data also suggest that low doses of TGFβ, could rescue PES-disrupted tube formation, suggesting inhibition of sEng activity.

EXAMPLE 9

Rescue of PE Serum-Induced Disruption of Cross-Talk by Growth Factors and Hormones $2.5 \times 10^4$ labeled endothelial and $2.5 \times 10^4$ HTR8 trophoblast cells were co-cultured on matrigel 12-14 hours and stimulated with either severe or mild PE serum, with or without 10 U/ml Heparin, 100 ng/ml Vascular Endothelial Growth Factor A (VEGF A), 100 ng/ml Vascular Endothelial Growth Factor C (VEGF C) or 10 mg/ml human chorionic gonadotropin (hCG) After 12-14 hours, the signature pattern of architectural morphology and number of tubes/vacuoles were recorded. The results are shown in FIG. 11 in which the graphic representation in FIG. 11a indicates the average number of tubes formed by the co-cultured, severe PE stimulated (L1015, L1020 refer to Table 1), mild PE stimulated (L1024, L1027) cells compared to the average number of tubes formed by the co-cultured, NPS stimulated (L32), cells. As seen in FIG. 11, NPS support the vacuolization while severe and mild PES disrupt the cross-talk. Co-incubation of mild PE serum with heparin can rescue the disrupted tube formation. Complement activity is generally inactivated by heat treatment. As indicated in FIG. 11, heat inactivated mild and severe PE serum samples supported tube formation, supporting the notion that complement factors are potential targets malleable to therapeutic intervention. Furthermore, these results indicate that exogenous addition of pro-angiogenic recombinant proteins like VEGF A and VEGF C can indeed rescue inhibition of tube formation by PES, implying that shallow trophoblast invasion and poor angiogenesis observed in preeclampsia are due to lack of such factors in PES. Furthermore, hCG though elevated in PE, does not seem to be functional. Using recombinant hCG, we show in FIG. 11b, PES-induced disruption can be rescued by exogenous hCG. In FIG. 11b, copies of exemplary photographs of the co-cultures are shown.

EXAMPLE 10

Humanized Mouse Model for Predicting Hypertensive Disorders

The anti-inflammatory cytokine IL-10 plays a critical role in pregnancy because of its regulatory relationship with other intrauterine modulators and its wide range of immunosuppressive activities. Significantly, its local production by gestational tissues is well documented. We have demonstrated that IL-10 expression by the human placenta was gestational age-dependent, with significant expression through the second trimester followed by attenuation at term. IL-10 expression was also found to be poor in decidual and placental tissues from unexplained spontaneous abortion cases, and from deliveries associated with preterm labor and preeclampsia (our unpublished observations). However, the mechanism(s) by which IL-10 protects the fetus remains poorly understood; IL-10$^{-/-}$ mice suffer no pregnancy defects unless challenged with inflammatory agents. Since PES is able to disrupt trophoblast and endothelial cell functions, we hypothesize that IL-10$^{-/-}$ mice could provide a model system to establish a "humanized" model to study onset of preeclampsia like systems in mice.

Pregnant wild type or IL-10-/- mice (C57BL/6, Jackson Labs, USA) were injected intraperitoneally on gestational day (gd) 10 with human normal pregnancy serum (NPS) or mild or severe PE serum (PES). On gd 16/17, urine and serum were collected from each mouse and blood pressure measurements were taken. Total urinary albumin was measured using Albumin (mouse) ELISA kit (ALPCO Diagnostics, Salem, N.H.) and urinary creatinine was measured using Metra Creatinine Kit (Quidel Corporation, San Diego, Calif.). Proteinuria is represented as the ratio of urinary albumin to creatinine (expressed as µg/mg). The baseline values seen in mice ranges from 100-400 µg/mg. Blood pressure was examined by an established tail-cuff method which utilizes a programmed sphygmomanometer. The animals adapted for 5 min using a warming test chamber (IITC Life Science Inc, Woodland Hills, Calif.) at controlled temperature (35° C.). The measurements were carried out on day 17 of pregnancy using DigiMed blood pressure analyzer, (MicroMed, 8008 Vine Crest Avenue, Suite 3, Louisville, Ky., 40222-4683). Each measurement of blood pressure is an average of three readings at 1 min interval from a number of animals (~3-5 each). Systolic blood pressure was compared among non pregnant and pregnant mice. All animals were age matched. Data was analyzed using Digi-Med® System Integrator™ Model 400 (DMSI-400). The data are provided in Tables 3 & 4.

TABLE 3

Effect of intraperitoneal injection of normal pregnancy serum and PE serum on BP, number of fetus and fetal weight, urine levels of proteinuria and serum levels of sFlt-1 and sEng levels in IL10 knockout mice.

|  | sFlt-1 (ng/ml) | sEndoglin (ng/ml) | Systolic BP (mmHg) | Proteinurea (ug/mg) | Aev Fetal Wt (g) | # Fetus |
|---|---|---|---|---|---|---|
| NPS (n = 9) | 61.25 ± 21.69 | 191.41 ± 45.31 | 93.46 ± 3.3 | 145.68 ± 58.96 | 1.24 ± 0.04 | 9 ± 0.81 |
| Severe PE Serum (n = 4) | 104.2 ± 28.7* | 395.31 ± 33.1* | 128.0 ± 12.9* | 391.89 ± 121.39* | 0.91 ± 0.12* | 8 ± 2 |
| Mild PE Serum (n = 4) | 55.29 ± 6.10 | 210.2 ± 24.2 | 113.48 ± 6.61* | 264.01 ± 94.8* | 1.23 ± 0.09 | 9 |

TABLE 4

Effect of intraperitoneal injection of normal pregnancy serum and PE serum on BP, number of fetus and fetal weight, urine levels of proteinuria and serum levels of sFlt-1 and sEng levels in wild type mice.

|  | sFlt-1 (ng/ml) | sEndoglin (ng/ml) | Systolic BP (mmHg) | Proteinurea (ug/mg) | Aev Fetal Wt (g) | # Fetus |
|---|---|---|---|---|---|---|
| NPS (n = 8) | 68.8 + 21.6 | 176.5 + 148.4 | 102.7 + 28.1 | 387.28 + 162.9 | 1.27 + 0.09 | 8.33 + 1.5 |
| SeverePE Serum (n = 4) | 51.9 + 28.18 | 379.4 + 172.3* | 147.4 + 18.9* | 828.5 + 570.9* | 1.0 + 0.25 | 7.6 + 1.51 |
| MildPE Serum (n = 4) | 75.57 + 14.3 | 200.2 + 21.2 | 101.9 + 17.58 | 228.4 + 24.2 | 1.07 + 0.1 | 8 + 0 |

The results of the study summarized in Tables 3 & 4 suggest that a number of PE serum samples representing mild and severe phenotypes induced some or all PE-associated symptoms when injected i.p. on gestational day (gd) 10 in IL10 null C57 BL/6 ((IL10$^{-/-}$) and wild type mice. The effects in response to only one administration of serum (100 µl) were evaluated on gd 17. Signature PE symptoms including intrauterine growth restriction (IUGR) as reflected by reduced fetal weight, elevated systolic blood pressure (BP), proteinuria, and elevated sFlt-1 and sEng levels were observed in response to severe PE serum and mild PE serum when compared to normal pregnancy serum (NPS). Significantly, severe PE serum samples had no effect on blood pressure and proteinuria in non-pregnant mice (data not shown). The high sensitivity and specificity of IL10 knockout mice to predict preeclampsia is reinforced by the fact that mild preeclampsia serum can induce hallmark symptoms of elevated blood pressure and proteinuria only in these mice but not in wild type animals. Statistical significance was assessed using Student's paired t-test. Differences were considered to be statistically significant when the p value was <0.05.

On gd 17 the mice were euthanized, the uterine horns were extracted and photographed and pregnancy outcomes were recorded. Serum sFlt-1, and sEng were measured by ELISA using commercially available kits. Exemplary results are shown in FIG. 12 in which the upper left and right panels are photographic reproductions of the uterine horns from IL-10 null and wild-type mice administered NPS, and the lower left and right panels are photographic reproductions of the uterine horns from IL-10 null and wild-type mice administered severe PE serum [(100 µl). Black arrows indicate sites of fetal resorption. As seen in the photographs, PE serum induced intrauterine growth restriction (IUGR in FIG. 12) and fetal resorption in IL-10 knockout mice, and not in wild-type mice.

All patents, publications, and other references cited herein are hereby incorporated by reference. Although the invention has been particularly described with reference to certain preferred embodiments, skilled artisans appreciate that changes in form and details may be made without departing from the scope of the appended claims.

REFERENCES

1. Matzuk M M, Burns K H, Viveiros M M, Eppig J J. Intercellular communication in the mammalian ovary: oocytes carry the conversation. Science 2002; 296:2178-2180
2. Paria B C, Reese J, Das S K, Dey S K. Deciphering the cross-talk of implantation: advances and challenges. Science 2002; 296:2185-2188
3. Abrams B, Pickett K E. Maternal Nutrition. In: Creasy R K, Resnik R, editors. Maternal-Fetal Medicine, 4th edn. Philadelphia, Pa.: W.B. Saunders Company; 1999; 122-131
4. Medawar P B. Some immunological and endocrinological problems raised by the evolution of viviparity in vertebrates. Symp. Soc. Exp. Biol. 1953; 7:320-338
5. Redman C W, Sargent I L. Preeclampsia, the placenta and the maternal systemic inflammatory response—a review. Placenta 2003; 24 Suppl A:S21-27
6. Kogevinas M. Human health effects of dioxins: cancer, reproductive and endocrine system effects. Hum Reprod Update. 2001; 7(3):331-339
7. Longenecker R. The Silver Lining. J Fam Pract. 2001; 50(6):552.
8. Morris J M, Gopaul N K, Endresen M J, Knight M, Linton E A, Dhir S, Anggard E E, Redman C W. Circulating markers of oxidative stress are raised in normal pregnancy and preeclampsia. Br J Obstet. Gynaecol. 1998; 105(11): 1195-9.
9. Gratacos E, Casals E, Deulofeu R, Cararach V, Alonso P L, Fortuny A. Lipid peroxide and vitamin E patterns in pregnant women with different types of hypertension in pregnancy. Am J Obstet. Gynecol. 1998; 178(5):1072-6.
10. Roberts J M. Endothelial dysfunction in preeclampsia. Sem Reprod Endocrinol 1998; 16:5-15.
11. Redman C W G, Sacks G P, Sargent I L. Preeclampsia, an excessive maternal inflammatory response to pregnancy. Am J Obstet Gynecol 1999; 180:499-506.
12. Bock W J. Ecological aspects of the evolutionary process. Zoolog Sci 2003; 20:279-289.
13. Murphy S P, Fast L D, Hanna N N, Sharma S. Uterine N K Cells Mediate Inflammation-Induced Fetal Demise in IL-10-Null Mice. J Immunology, 2005; 175:4084-4090.
14. Hayakawa S, Fujikawa T, Fukuoka H, Chisima F, Karasaki-Suzuki M, Ohkoshi E, Ohi H, Kiyoshi Fujii T, Tochigi M, Satoh K, Shimizu T, Nishinarita S, Nemoto N, Sakurai I. Murine fetal resorption and experimental preeclampsia are induced by both excessive Th1 and Th2 activation. J Reprod Immunol 2000; 47:121-38.
15. Takimoto E, Ishida J, Sugiyama F, Horiguchi H, Murakami K, Fukamizu A. Hypertension induced in pregnant mice by placental renin and maternal angiotensinogen. Science 1996; 274:995-8
16. Kanayama N, Takahashi K, Matsuura T, Sugimura M, Kobayashi T, Moniwa N, Tomita M, Nakayama K. Deficiency in p57kip2 expression induces preeclampsia-like symptoms in mice. Mol Human Reprod 2002; 8:1129-1135.
17. Davisson R L, Hoffmann D S, Butz G M, Aldape G, Schlager G, Merrill D C, Sethi S, Weiss R M, Bates J N. Discovery of a spontaneous genetic mouse model of preeclampsia. Hypertension 2002; 39:337-42.
18. Venkatesha S, Toporsian M, Lam C, Hanai J, Mammoto T, Kim Y M, Bdolah Y, Lim K H, Yuan H T, Libermann T A, Stillman I E, Roberts D, D'Amore P A, Epstein F H, Sellke F W, Romero R, Sukhatme V P, Letarte M, Karumanchi S A. Soluble endoglin contributes to the pathogenesis of preeclampsia. Nat. Med. 2006; 12(6):642-9.
19. Widmer M, Villar J, Benigni A, Conde-Agudelo A, Karumanchi S A, Lindheimer M. Mapping the theories of preeclampsia and the role of angiogenic factors: a systematic review. Obstet. Gynecol. 2007; 109(1):168-80.
20. DiFederico E, Genebacev O, Fisher S J. Preeclampsia is associated with widespread apoptosis of placental cytotrophoblasts within the uterine wall. Am J Pathol 1999; 155: 293-301.
21. Genebacev O, DiFederico E, McMaster M, et al. Invasive cytotrophoblast apoptosis in preeclampsia. Hum Reprod 1999; 14 (suppl 2):59-66.
22. Leung D N, Smith S C, To K F, et al. Increased placental apoptosis in pregnancies complicated by preeclampsia. Am J Obstet Gynecol 2001; 184:1249-1250.
23. Balkundi D R, Hanna H, Hleb M, Dougherty J, Sharma S. Labor-associated changes in Fas ligand expression and function in human placenta. Pediatr Res 2000; 47:301-308.
24. Peracoli J C, Rudge M V, Peracoli M T. Tumor necrosis factor-alpha in gestation and puerperium of women with gestational hypertension and preeclampsia. Am J Reprod Immunol. 2007; 57(3):177-185.
25. Jonsson Y, Ruber M, Matthiesen L, Berg G, Nieminen K, Sharma S, Ernerudh J, Ekerfelt C. Cytokine mapping of sera from women with preeclampsia and normal pregnancies. J Reprod Immunol. 2006; 70(1-2):83-91.

26. Banerjee S, Smallwood A, Moorhead J, Chambers A E, Papageorghiou A, Campbell S, Nicolaides K. Placental expression of interferon-gamma (IFN-gamma) and its receptor IFN-gamma R2 fail to switch from early hypoxic to late normotensive development in preeclampsia. J Clin Endocrinol Metab. 2005; 90(2):944-952.
27. Hendler I, Blackwell S C, Mehta S H, Whiny J E, Russell E, Sorokin Y, Cotton D B. The levels of leptin, adiponectin, and resistin in normal weight, overweight, and obese pregnant women with and without preeclampsia. Am J Obstet. Gynecol. 2005; 193(3 Pt 2):979-83.
28. Shah D M. Role of the renin-angiotensin system in the pathogenesis of preeclampsia. Am J Physiol Renal Physiol. 2005; 288(4):F614-625.
29. Salmon J E, Girardi G. Antiphospholipid antibodies and pregnancy loss: A disorder of inflammation. J Reprod Immunol. 2007 Apr. 4; [Epub ahead of print]
30. Girardi G, Redecha P, Salmon J E. Heparin prevents antiphospholipid antibody-induced fetal loss by inhibiting complement activation. Nat. Med. 2004; 10 (11):1222-6.
31. Sharma A, Satyam A, Sharma J B. Leptin, IL-10 and Inflammatory Markers (TNF-alpha, IL-6 and IL-8) in Pre-Eclamptic, Normotensive Pregnant and Healthy Non-Pregnant Women. Am J Reprod Immunol. 2007; 58(1):21-30.
32. See Ananth et al., Placental Abruption and Adverse Perinatal Outcomes, JAMA. 1999; 282:1646-1651.
33. Withington, "A High-Throughput Screening Assay to Quantitate Drug-induced Inhibition of Endothelial Tube Formation, BD Biosciences, 2001.
34. Jones R M, Boatman P D, Semple G, Shin Y J, Tamura S Y. Clinically validated peptides as templates for de novo peptidomimetic drug design at G-protein-coupled receptors, Curr Opin Pharmacol. 2003 October; 3(5):530-43.

The invention claimed is:

1. An assay for assessing whether a pregnant female is at risk of developing a pregnancy disorder characterized by either poor trophoblast invasion or placental ischemia, or both, comprising (a) incubating a co-culture of human endothelial cells and human trophoblast cells in the presence of serum obtained from the pregnant female for a period of time sufficient to permit vacuolization, (b) after incubation, determining whether substantial vacuolization in the co-culture has occurred and (c) if less than said substantial vacuolization has occurred, the pregnant female is determined to have a positive finding for risk of developing said pregnancy disorder.

2. The assay according to claim 1 wherein the disorder is selected from preeclampsia, gestational diabetes, intrauterine growth restriction, and trophoblastic diseases with hyper- or hypo invasive features.

3. The assay according to claim 2, additionally comprising the steps of incubating a co-culture of human endothelial cells and human trophoblast cells under the same conditions as the co-culture in claim 1 (a) in the absence of serum or plasma from a pregnant female for a period of time sufficient to permit vacuolization and after incubation determining whether substantial vacuolization in either co-culture has occurred.

4. The assay according to claim 1 wherein incubation time is at least 12 hours.

5. The assay according to claim 4 wherein the serum is from the first trimester of the pregnant female's pregnancy.

6. The assay according to claim 5 wherein the amount of serum used is 0.05-2 ml.

7. The assay according to claim 6 wherein the endothelial cells are selected from umbilical vein, uterine, myometrial, decidual, aorta, microvascular, dermal or other endothelial cells that express VE-cadherin, PECAM, and/or Aquaporin 1.

8. The assay according to claim 6 wherein the trophoblasts are selected from primary villous or extravillous trophoblasts, HTR8 and 3A trophoblasts or other invasive trophoblasts isolated from choriocarcinomas.

9. The assay according to claim 7 wherein the co-culture is performed on a natural or synthetic soluble matrix.

10. The assay according to claim 9 wherein the matrix is selected from matrigel, collagen, fibronectin, elastin and combinations thereof.

11. The assay according to claim 10 wherein the incubation step is performed at 37° C. in carbon dioxide.

12. An assay for assessing whether a pregnant female is at risk of developing a pregnancy disorder characterized by either poor trophoblast invasion or placental ischemia, or both, comprising (a) incubating a co-culture of human endothelial cells and human trophoblast cells in the presence of serum obtained from e the pregnant female for a period of time sufficient to permit vacuolization, (b) after incubation, determining whether substantial vacuolization in the co-culture has occurred and (c) if said substantial vacuolization is present, the pregnant female is determined to have a negative finding for risk of developing said pregnancy disorder.

\* \* \* \* \*

UNITED STATES PATENT AND TRADEMARK OFFICE
CERTIFICATE OF CORRECTION

| | | |
|---|---|---|
| PATENT NO. | : 9,176,120 B2 | Page 1 of 1 |
| APPLICATION NO. | : 12/865239 | |
| DATED | : November 3, 2015 | |
| INVENTOR(S) | : Surendra Sharma et al. | |

It is certified that error appears in the above-identified patent and that said Letters Patent is hereby corrected as shown below:

IN THE CLAIMS

Column 20, Claim 12, line 40, "e the" should be --the--.

Signed and Sealed this
Twenty-second Day of March, 2016

Michelle K. Lee
*Director of the United States Patent and Trademark Office*